US012446934B2

(12) United States Patent
Bomar et al.

(10) Patent No.: US 12,446,934 B2
(45) Date of Patent: Oct. 21, 2025

(54) SYSTEMS AND METHODS OF BONE PLATING

(71) Applicant: MiRus LLC, Marietta, GA (US)

(72) Inventors: Bradley Bomar, Marietta, GA (US); Wayne Gray, Mableton, GA (US); Noah Roth, Marietta, GA (US); Kaitlin Jones James, Atlanta, GA (US); Dennis Moreno, Marietta, GA (US)

(73) Assignee: MiRus LLC, Marietta, GA (US)

( * ) Notice: Subject to any disclaimer, the term of this patent is extended or adjusted under 35 U.S.C. 154(b) by 268 days.

(21) Appl. No.: 18/098,376

(22) Filed: Jan. 18, 2023

(65) Prior Publication Data

US 2023/0255669 A1 Aug. 17, 2023

Related U.S. Application Data

(63) Continuation-in-part of application No. 29/852,595, filed on Sep. 8, 2022, now Pat. No. Des. 1,039,696, and a continuation-in-part of application No. 29/852,274, filed on Sep. 6, 2022, now Pat. No. Des. 1,039,152, and a continuation-in-part of application No. 29/852,303, filed on Sep. 6, 2022, now Pat. No. Des. 1,041,008.

(60) Provisional application No. 63/407,823, filed on Sep. 19, 2022, provisional application No. 63/300,452, filed on Jan. 18, 2022.

(51) Int. Cl.
*A61B 17/80* (2006.01)
*A61L 31/02* (2006.01)

(52) U.S. Cl.
CPC ...... *A61B 17/8052* (2013.01); *A61B 17/8085* (2013.01); *A61L 31/022* (2013.01)

(58) Field of Classification Search
CPC . A61B 17/80; A61B 17/8052; A61B 17/8085; A61L 31/022
See application file for complete search history.

(56) References Cited

U.S. PATENT DOCUMENTS

| | | | |
|---|---|---|---|
| 6,306,136 B1 | 10/2001 | Baccelli | |
| 6,602,256 B1 | 8/2003 | Hayes | |
| 6,602,257 B1 | 8/2003 | Thramann | |
| 6,679,883 B2 | 1/2004 | Hawkes et al. | |
| 7,066,961 B2 | 6/2006 | Michelson | |
| 7,220,263 B2 | 5/2007 | Cordaro | |
| 7,306,605 B2 | 12/2007 | Ross | |
| 7,318,825 B2 | 1/2008 | Butler et al. | |
| 7,815,666 B2 | 10/2010 | Baynham et al. | |
| 8,328,854 B2 | 12/2012 | Baynham et al. | |
| 8,778,001 B2 | 7/2014 | Thramann et al. | |
| 8,961,517 B2 | 2/2015 | McClintock et al. | |
| 9,149,311 B2 | 10/2015 | Elsbury | |
| 9,629,664 B2 | 4/2017 | Altarac et al. | |
| 9,814,495 B2 | 11/2017 | Robie | |
| 9,844,402 B2 | 12/2017 | Mayer et al. | |
| 10,258,395 B2 * | 4/2019 | Pak | A61B 17/8052 |
| 10,912,591 B2 | 2/2021 | Altarac et al. | |
| 2011/0015681 A1 * | 1/2011 | Elsbury | A61B 17/7059 606/281 |
| 2019/0117827 A1 * | 4/2019 | Roth | A61L 31/022 |

* cited by examiner

*Primary Examiner* — Si Ming Ku
(74) *Attorney, Agent, or Firm* — UB Greensfelder LLP; Brian E. Turung

(57) ABSTRACT

An orthopedic fixation device and bone plating system for fracture fixation and methods for using the bone plating systems.

12 Claims, 10 Drawing Sheets

SYSTEMS AND METHODS OF BONE PLATING

The present disclosure claims priority in U.S. Provisional Application Ser. No. 63/407,823 filed Sep. 19, 2022, which is incorporated herein by reference.

The present disclosure claims priority in U.S. Provisional Application Ser. No. 63/300,452, filed Jan. 18, 2022, which is incorporated herein by reference.

The present disclosure is a continuation-in-part of U.S. application Ser. No. 29/852,595 filed Sep. 8, 2022, which is incorporated herein by reference.

The present disclosure is a continuation-in-part of U.S. application Ser. No. 29/852,303 filed Sep. 6, 2022, which is incorporated herein by reference.

The present disclosure is a continuation-in-part of U.S. application Ser. No. 29/852,274 filed Sep. 6, 2022, which is incorporated herein by reference.

The disclosure relates generally to medical devices and medical device applications, more particularly to orthopedic devices, and still more particularly to orthopedic fixation devices and bone plating systems for fracture fixation and methods for using the bone plating systems.

BACKGROUND

Bone fractures can be repaired by securing a bone plate across the fracture. The bone plate may be straight or curved to match the contour of the bone to be repaired. The use of a bone plate promotes healing of the fracture by providing a rigid fixation or support structure between the bone and the plate.

Bone plates can be secured to the bone by use of a screw system wherein the screws are locked in the plate. A bone screw is generally threaded through an opening in the plate and into the bone. The screw can be secured to the bone plate by the threads on the head of the screw. Locking a screw into the plate can achieve angular and axial stability and eliminate the possibility for the screw to toggle, slide, or be dislodged.

Another type of screw system uses non-locking screws that are secured into bone, but not secured to the plate. One advantage of non-locking screws is they can be inserted at various angles because they are not limited by the thread-to-thread contact of locking screws with the bone plate.

There are also bone plates that use both locking and non-locking screws to secure the plate to the bone. These types of bone plates typically include a partially threaded opening that can receive either a compression screw or a locking screw.

Another type of bone plate utilizes polyaxial fixation arrangement. Such prior art bone plates are illustrated and described in U.S. Pat. No. 10,327,822 and WO 2005/018472; and also illustrated in FIG. 1, all of which are fully incorporated herein by reference.

In view of the current state of the art, it would be desirable to provide a thinner bone plate without sacrificing the strength of typically thicker bone plates formed of stainless steel or cobalt-chromium alloys, and which includes a locking feature that can lock the head of the screw to the plate at many different screw angles relative to the bone plate.

SUMMARY OF THE DISCLOSURE

The present disclosure is direct to a medical device in the form of an orthopedic fixation device and bone plating system for fracture fixation and methods for using the bone plating systems. The bone plates can be used on various bones such as, but not limited to, a radius, an ulna, spinal bones, maxillofacial bones, a fibula, metatarsal bones, calcaneus bones, ankle bones, femur, distal tibia, proximal tibia, proximal humerus, distal humerus, a clavicle, bones of the foot, bones of the hand, etc.

In one non-limiting aspect of the disclosure, there is provided a medical implant which fixates portions of bone together to facilitate bone fusion. More specifically, the medical device is in the form of a bone plate made of a metal alloy (e.g., refractory metal alloy, metal alloy that includes at least 15 awt. % rhenium, etc.) and configured to be used with a fastening system, such as screws, that are configured to penetrate and affix the bone plate to a bone while enabling multiple directions of the screw axis relative to the normal vector of the bone plate, which facilitates fusion by stabilizing sections of bone together. The bone plate is configured to stabilize and aid in the repair of fractures, fusions, and osteotomies of bones in adult and pediatric patients. The bone plate allows for a wide range of screw-locking angulation, thus providing greater surgical options during bone repairing procedures. In use, the bone plate is placed on the surface of the two portions of bone that are desired to be fused.

In another and/or alternative non-limiting aspect of the disclosure, the geometry of the screw openings in the bone plate optionally allows for plastic deformation of the screw opening geometry to lock the head of the screw in the screw opening. This locked construct of the screw head and screw opening in the bone plate can be used to stabilize the bones relative to the bone plate and facilitate fusion.

In another and/or alternative non-limiting aspect of the disclosure, the bone plate in accordance with the present disclosure is configured to accept a fastener arrangement (e.g., screws, etc.). As defined herein, a bone fixation assembly includes the bone plate in accordance with the present disclosure and the fastener arrangement (e.g., one or more screws, etc.). The bone plate includes an upper surface, a lower surface, a central longitudinal axis, a lateral axis that is traverse to the central longitudinal axis, and a plurality of screw openings that pass fully through the bone plate. The shape and/or size of the screw openings can be the same or different. In one non-limiting embodiment, the shape and size of a plurality or all of the screw openings are the same. The spacing of adjacently positioned screw openings can be the same or different. In one non-limiting embodiment, the spacing of three or more adjacently positioned screw openings is the same. One or more or all of the screw openings are spaced from the peripheral edge of the bone plate. In one non-limiting embodiment, all of the screw openings are spaced from the peripheral edge of the bone plate.

In another and/or alternative non-limiting aspect of the disclosure, the one or more screw openings in the bone plate can optionally have a generally circular cross-sectional shape and the inner surface of the screw openings can optionally include a series of inwardly-protruding surfaces. In one non-limiting embodiment, the plurality of protruding surfaces extend into screw opening toward the central axis of the screw opening and are spaced from the central axis of the screw opening. In another non-limiting embodiment, the plurality of protruding surfaces are smooth and non-threaded. One non-limiting purpose of the plurality of protruding surfaces is to engage one or more threads on the head of a fastener arrangement (e.g., screw, etc.) to facilitate in securing the head of the fastener arrangement to the bone plate. In one non-limiting embodiment, one or more of the protruding surfaces are configured to be plastically deformed when the head of the fastener arrangement is partially or fully inserted into the screw opening. The plastic deformation and frictional engagement between the head of the screw and the protruding surfaces results in the head of the fastener arrangement being secured to the bone plate when the fastener arrangement is fully inserted into the screw openings. In one non-limiting arrangement, the screw opening is absent threads and only the plastic deformation and frictional engagement between the head of the screw and the protruding surfaces is used to secure the head of the fastener arrangement to the bone plate. In such an arrangement, the head of the fastener arrangement may or may not include threading since any threading on the head of the fastener arrangement will not be engaging any thread in the screw opening. In one non-limiting embodiment, one or more of the screw openings include a plurality of protruding surfaces (e.g., 2-16 and all values therebetween, 4, 6, 8, 10, 12, etc.) when the screw opening is viewed along its central axis. In another non-limiting embodiment, when the screw opening is viewed along its central axis, an arcuate recessed region is located on both sides of the protruding surface. In another non-limiting embodiment, each of the protruding surfaces and arcuate recessed regions are formed by a plurality of adjacently positioned sloped surfaces. Each of the sloped surfaces extends no more than 10% (e.g., 2-10% and all values and ranges therebetween) about a perimeter of the screw opening. In another non-limiting embodiment, there are provided top and bottom and intermediate sloped surfaces. In one non-limiting arrangement, the top sloped surfaces slope downwardly from a top edge or a top region of the screw opening and terminate at a location that is ±0-20% (and all values and ranges therebetween) the mid-depth of the screw opening. In one non-limiting arrangement, the bottom sloped surfaces slope upwardly from a bottom edge or a bottom region of the screw opening and terminate at a location that is ±0-20% (and all values and ranges therebetween) the mid-depth of the screw opening. In one non-limiting arrangement, a plurality of top sloped surfaces and a plurality of bottom sloped surfaces have a similar shape and/or a similar size. In one non-limiting arrangement, a first top sloped surfaces is positioned above a first bottom sloped surface and the first top and bottom slope surfaces form a first protruding surface, and a second top sloped surfaces is positioned above a second bottom sloped surface and the second top and bottom slope surfaces form a second protruding surface, and a first intermediate sloped surface is positioned between the pair of first top and bottom slope surfaces and second top and bottom slope surfaces. In another non-limiting arrangement, one or more of the top sloped surfaces have three sides in another non-limiting arrangement, one or more of the bottom sloped surfaces have three sides. In another non-limiting arrangement, one or more of the intermediate sloped surfaces have four sides. In another non-limiting arrangement, one or more of the intermediate sloped surfaces extends from the top edge or the top region of the screw opening to the bottom edge or the bottom region of the screw opening. In another non-limiting arrangement, one or more of the screw openings is absent a thread.

In another and/or alternative non-limiting aspect of the disclosure, the inner surface of the one or more screw openings optionally has a special threaded configuration that enables the head portion of the fastener arrangement to be locked in the screw opening once the head portion of the fastener arrangement is fully inserted into the screw opening One or more of the screw openings includes a lead thread plate that includes a plurality of lead recesses, and wherein the lead recesses are spaced from one another. The plurality of lead recesses is configured to facilitate in the threading of the head of the fastener arrangement to the screw opening. In one non-limiting embodiment, the minimum width of one or more of the lead recesses is less than a maximum width of a bottom thread located below the lead thread plate. In one non-limiting embodiment, the maximum width of one or more portions of the lead thread plate is greater than a maximum width of a bottom thread located below the lead thread plate.

In another and/or alternative non-limiting aspect of the disclosure, the inner surface of the one or more screw openings includes one or more sets of lower threading located below the bottom surface of the lead thread plate. In one non-limiting embodiment, the one or more lower threading forms a spiral surface that has a generally uniform thread width and thickness along the depth of the screw opening. In another non-limiting embodiment, one or more of the lower threading does not fully encircle the screw opening (e.g., lower threading encircles 30-90% of the screw opening and all values and ranges therebetween). In another non-limiting embodiment, one or more screw openings includes a lead thread plate that includes first and second lead recesses and a first bottom thread that begins below the first lead recess and a second bottom thread begins below the second lead recess, and wherein the first and/or second bottom threads optionally do not fully encircle the screw opening, and wherein the lead recesses are spaced equal distances from adjacently positioned lead recesses. In another non-limiting embodiment, one or more screw openings includes a lead thread plate that includes first, second, and third lead recesses and a first bottom thread that begins below the first lead recess, a second bottom thread begins below the second lead recess, and a third bottom thread begins below the third lead recess, and wherein the first, second, and/or third bottom threads optionally do not fully encircle the screw opening, and wherein the lead recesses are optionally spaced equal distances from adjacently positioned lead recesses.

In another and/or alternative non-limiting aspect of the disclosure, the lead thread plate has a certain lead and pitch that can be less than the lead and pitch of the threading on one or more portions of the fastener arrangement.

In another and/or alternative non-limiting aspect of the disclosure, the lead thread plate is recessed from the top surface of bone plate. The depth of the recess is at least 0.002 inches (e.g., 0.002-0.025 and all values and ranges therebetween), and typically at least 0.005 inches. Generally, the depth of the recess is at least 5% (e.g., 5-60% and all values and ranges therebetween) of the thickness of screw opening, and typically the depth of the recess is at least 15% of the thickness of screw opening. The recessed region has a generally circular cross-sectional shape; however, this is not required. In one non-limiting embodiment, the diameter or cross-sectional area of the screw opening located above lead thread plate is greater than the maximum diameter or cross-sectional area of the bottom thread located below the lead thread plate.

In another and/or alternative non-limiting aspect of the disclosure, the length of the effective bottom thread along the central axis of the screw opening is at least 25% (e.g., 25-90% and all values and ranges therebetween) of the thickness of screw opening.

In another and/or alternative non-limiting aspect of the disclosure, the bone plate includes one or more non-threaded screw openings. In one non-limiting embodiment, the one or more non-threaded screw openings are absent a lead thread plate and a bottom thread. In another non-limiting embodiment, the one or more non-threaded screw openings have a maximum cross-sectional area along the longitudinal length of the bone plate that is greater than a maximum cross-sectional area of the screw openings that include a lead thread plate and a bottom thread. In another non-limiting embodiment, the one or more non-threaded screw openings are positioned between screw openings that include threads. In another non-limiting embodiment, the one or more non-threaded screw openings have a sloped surface that slopes downwardly from a top surface of the bone plate and have a thickness of 50-100% (and all values and ranges therebetween) of the thickness of the bone plate. In another non-limiting embodiment, the sloped surface of the one or more non-threaded screw openings does not fully encircle the non-threaded screw opening.

In another and/or alternative non-limiting aspect of the disclosure, the bone plate can be shaped to match a particular bone surface (e.g., I-shaped, L-shape, T-shape, Y-shape, S-shape, C-shaped, E-shaped, F-shaped, J-shaped, U-shaped, etc.) and any other appropriate shape to fit the bone to be treated. In one non-limiting embodiment the bone plate can have a planar or non-planar profile along the longitudinal length of the bone plate. In another non-limiting embodiment, the bone plate can have a planar or non-planar profile along the lateral axis of the bone plate along one or more locations or along the complete longitudinal length of the bone plate. The thickness of the bone plate can be constant or vary along the longitudinal length of the bone plate. In one non-limiting embodiment, the thickness of the bone plate is generally constant along 80-100% (and all values and ranges therebetween) of the longitudinal length of the bone plate. One or more surface of the bone plate can optionally be formed by a cutting process, stamping process, 3D printer, molding process, etc.

In another and/or alternative non-limiting aspect of the disclosure, the width of the bone plate can optionally vary along the longitudinal length of the bone plate. In one non-limiting embodiment, the width of the bone plate varies along the longitudinal length of the bone plate. In one non-limiting embodiment, one or both sides of the bone plate can optionally have multiple arcuate regions that create a generally wavy side or sinusoidal-shaped edges of the bone plate; however, it can be appreciated that such arcuate regions are not required. The radius of curvature of the wavy side edges is generally 5-10 mm (and all values and ranges therebetween), and typically 7-9 mm. Due to these arcuate regions, the width of the bone plate varies along the longitudinal length the bone plate. Generally, the location of the screw openings in the bone plate represent a larger width region of bone plate than the regions absent screw openings. In one non-limiting embodiment, the maximum width of the bone plate (as measured along the lateral axis of the bone plate) that includes one or more screw openings is 5-40% greater (and all values and ranges therebetween) than the minimum width of bone plate at a location between two screw openings.

In another and/or alternative non-limiting aspect of the disclosure, the bone plate can be optionally curved (e.g., 2+−10° and all values and ranges therebetween) about the central longitudinal axis of the bone plate. In one non-limiting embodiment, the bone plate is curved (e.g., 2+−8° and all values and ranges therebetween) about the central longitudinal axis of the bone plate, and the bone plate is generally planar (e.g., 0-2° and all values and ranges therebetween) along the central longitudinal axis of the bone plate. In another non-limiting embodiment, the bone plate is curved (e.g., 2+−8° and all values and ranges therebetween) about the central longitudinal axis of the bone plate, and the bone plate is curved (e.g., 2+−10° and all values and ranges therebetween) along the central longitudinal axis of the bone plate.

In another and/or alternative non-limiting aspect of the disclosure, the bone plate and/or the screw openings in the bone plate can be configured to enable a fastener arrangement to be oriented a) along the central axis of the screw opening when fully inserted into the screw openings, or b) be oriented off-center from the central axis of the screw opening when fully inserted into the screw openings. The bone plate having a plurality of screw openings with the same size and configuration can enable a) all of the fastener arrangement to be oriented in the same way relative to the central axis of the screw opening when fully inserted into the screw openings, or b) one or more of the fastener arrangements to have a different orientation to other fastener arrangements when fully inserted into the screw openings. The bone plate having a plurality of screw openings with the same size and configuration can also enable a) the central axis of all of the fastener arrangements to be parallel with one another when fully inserted into the screw openings, or b) the central axis of one or more of the fastener arrangements to be non-parallel (e.g., oriented inwardly toward one another, oriented outwardly from one another, etc.) with the central axis of one or more other fastener arrangements when fully inserted into the screw openings. The ability to enable the fastener arrangements to be secured to the bone plate in various orientations relative to the central axis of the bone while using the same screw opening configuration on the bone plate is a significant advantage when attempting to secure the bone plate to a bone since the desired location of insertion of the fastener arrangement to the bone when the bone plate is positioned on the bone is not always along the central axis of the screw opening. The ability to custom orient the fastener arrangement relative to the central axis of one or more or all of the screw openings enables the proper insertion of the fastener arrangement in the bone once the bone plate is properly positioned on the bone.

In another and/or alternative non-limiting aspect of the disclosure, the fastener arrangement can be any typical, standard locking fastener or a non-locking fastener (e.g., screw, post, screw with a threaded head, screw that is absent a threaded head, etc.). In one non-limiting embodiment, the fastener arrangement is a screw that includes a head portion and a body portion. The head portion generally has a maximum cross-sectional area greater than a maximum cross-sectional area of the body portion. The head portion may or may not include threads. Likewise, the body portion may or may not include threads. For example, the body portion can be fully threaded, partially threaded, comprise a helical blade, and/or may comprise one or more tacks, deployable talons, expanding elements, or so forth. As can be appreciated, the body of the fastener arrangement can be a peg or pin shape. The end region of the body portion can optionally include a self-tapping or self-drilling tip; however, this is not required. The shape of the head portion is non-limiting. In one non-limiting embodiment, the cross-sectional shape of the top region of the head portion is generally circular shaped; however, other shapes can be used. The head portion can optionally include a cavity to facilitate in inserting the fastener arrangement into a bone and securing the bone plate to the bone. The configuration of the cavity (when used) is non-limiting. Generally, the cavity is specially shaped to receive a tool to rotate and/or otherwise cause the fastener arrangement to be inserted into a bone. Non-limiting shapes that can be used in the cavity include one or more dimples, ridges, bumps, textured areas, star-shaped, polygonal-shaped, or any other surface or shape. As can be appreciated, the cavity can include a threaded inner surface and a circular cross-sectional shape.

In another and/or alternative non-limiting aspect of the disclosure, the fastener arrangement is a screw that includes a head portion and a body portion, the head portion generally has a maximum cross-sectional area that is greater than a maximum cross-sectional area of the body portion, 60-100% (and all values and ranges therebetween) of the longitudinal length of the head portion is absent threads, 60-100% (and all values and ranges therebetween) of the longitudinal length of the body portion includes spirally-shaped threads, the end region of the body portion optionally includes a self-tapping or self-drilling tip, the cross-sectional shape of the top region of the head portion is generally circular shaped along 60-100% (and all values and ranges therebetween) of the longitudinal length of the head portion, the cross-sectional shape of the bottom region of the head portion is generally circular shaped along 60-100% (and all values and ranges therebetween) of the longitudinal length of the head portion, and the head portion can optionally include a cavity to facilitate in inserting the fastener arrangement into a bone and securing the bone plate to the bone.

In another and/or alternative non-limiting aspect of the disclosure, the fastener arrangement is a screw that includes a head portion and a body portion, the head portion generally has a maximum cross-sectional area that is greater than a maximum cross-sectional area of the body portion, 60-100% (and all values and ranges therebetween) of the longitudinal length of the head portion includes threads, 60-100% (and all values and ranges therebetween) of the longitudinal length of the body portion includes spirally-shaped threads, the end region of the body portion optionally includes a self-tapping or self-drilling tip, the cross-sectional shape of the top region of the head portion is generally circular shaped along 60-100% (and all values and ranges therebetween) of the longitudinal length of the head portion, the cross-sectional shape of the bottom region of the head portion is generally circular shaped along 60-100% (and all values and ranges therebetween) of the longitudinal length of the head portion, and the head portion can optionally include a cavity to facilitate in inserting the fastener arrangement into a bone and securing the bone plate to the bone.

In another and/or alternative non-limiting aspect of the disclosure, the head portion of the fastener arrangement has a tapered profile that includes threading along 60-100% (and all values and ranges therebetween) of the central axis of the tapered portion of the head portion. The tapered portion of the head portion is generally 20-100% (and all values and ranges therebetween) of the longitudinal length of the head portion. The angle of taper is generally at least P (e.g., 1-25° and all values and ranges therebetween). As such, the cross-sectional area and/or diameter of the top region of the head portion that includes threading on the tapered region is greater than the cross-sectional area and/or diameter of the bottom region of the head portion that includes threading on the tapered region. In one non-limiting arrangement, the angle of taper of the head portion that includes threading is constant along 60-100% (and all values and ranges therebetween) of the taper. In another non-limiting arrangement, the threading on the head portion is spirally-shaped and has a) a constant width along 60-100% (and all values and ranges therebetween) the length of the threading, b) a constant shape along 60-100% (and all values and ranges therebetween) the length of the threading, c) a constant lead along 60-100% (and all values and ranges therebetween) the length of the threading, and/or d) a constant pitch along 60-100% (and all values and ranges therebetween) the length of the threading. The use of the tapered region on the head portion of the fastener arrangement can optionally facilitate in enabling the fastener arrangement to be oriented in the screw opening at a desired angle relative to the central axis of the screw opening. When the screw opening includes a lead thread plate having two or more recesses, the bottom narrower portion of the tapered region of the head portion of the fastener arrangement can be used to allow the fastener arrangement to be angled and positioned in the desired recess of the lead thread plate of the screw opening before the threads on the tapered region fully engage the lead thread plate and/or the threads below the lead thread plate.

In another and/or alternative non-limiting aspect of the disclosure, the fastener arrangement optionally includes a non-threaded transition region that is positioned between the threading on the upper portion of head portion and the threading on the top portion of the body portion. The non-threaded transition region of the head portion (when used) is generally 5-80% (and all values and ranges therebetween) of the longitudinal length of the head portion. In one non-limiting arrangement, the minimum cross-sectional area of the non-threaded transition region is less than the maximum cross-sectional area of the head portion and/or the body portion. The use of the non-threaded transition region on the head portion of the fastener arrangement optionally facilitate in enabling the fastener arrangement to be oriented in the screw opening at a desired angle relative to the central axis of the screw opening. When the screw opening includes a lead thread plate having two or more recesses, the non-threaded transition region of the head portion of the fastener arrangement can be used to allow the fastener arrangement to be angled and positioned in the desired recess of the lead thread plate of the screw opening before the threads on the taper region fully engage the lead thread plate and/or the threads below the lead thread plate.

In another and/or alternative non-limiting aspect of the disclosure, the threading on the head portion of the fastener arrangement generally has the same or similar lead and pitch as the threading in the screw opening in the bone plate.

In another and/or alternative non-limiting aspect of the disclosure, the threading on the body portion of the fastener arrangement includes threading having a different lead and pitch than the threading on the head portion of the fastener arrangement.

In another and/or alternative non-limiting aspect of the disclosure, the threading on the body portion of the fastener arrangement has a maximum cross-sectional area that is less than the minimum cross-sectional area of the screw opening so the body portion of the fastener arrangement can be passed through the screw opening.

In another non-limiting aspect of the present disclosure, the bone plate and/or fastener system that can be manufactured from any suitable biocompatible material, including metal, such as stainless steel, cobalt-chromium alloy, cobalt-chromium-molybdenum alloy, titanium-aluminum vanadium alloy, molybdenum titanium alloy, molybdenum rhenium alloy, molybdenum alloy, rhenium alloy, rhenium-chromium alloy, refractory metal alloy, rhenium-containing alloy, or other suitable metallic alloys. In accordance with one non-limiting embodiment, the bone plate and/or fastener system is formed of 50-100% (and all values and ranges therebetween) of the suitable biocompatible material.

In accordance with another and/or alternative non-limiting aspect of the present disclosure, there is provided a bone plate and/or fastener system partially or fully formed of a metal alloy that includes rhenium in a sufficient quantity as to create a "rhenium effect" in the metal alloy. As defined herein, a "rhenium effect" is a) an increase of at least 10% in ductility of the metal alloy caused by the addition of rhenium to the metal alloy, and/or b) an increase of at least 10% in tensile strength of the metal alloy caused by the addition of rhenium to the metal alloy. It has been found for many metal alloys (e.g., standard stainless steel, standard CoCr alloys, standard TiAlV alloys, standard aluminum alloys, standard nickel alloys, standard titanium alloys, standard tungsten alloys, standard molybdenum alloys, standard coper alloys, standard MP35N alloys, standard beryllium-copper alloys, etc.) results in improved ductility and/or tensile strength. It has been found that the addition of rhenium to a metal alloy can result in the formation of a twining alloy in the metal alloy that results in the overall ductility of the metal alloy to increase as the yield and tensile strength increases due to the reduction and/or work hardening of the metal alloy. The rhenium effect occurs when the atomic weight of rhenium in the metal alloy is at least 15% (e.g., 15-99 awt. % rhenium in the metal alloy and all values and ranges therebetween). For example, for standard stainless steel alloys, the rhenium effect can begin to be present when the stainless steel alloy is modified to include a rhenium amount of at least 5-10 wt. % (and all values and ranges therebetween) of the stainless steel alloy. For standard CoCr alloys, the rhenium effect can begin to be present when the CoCr alloy is modified to include a rhenium amount of at least 4.8-9.5 wt. % (and all values and ranges therebetween) of the CoCr alloy. For standard TiAlV alloys, the "rhenium effect" can begin to be present when the TiAlV alloy is modified to include a rhenium amount of at least 4.5-9 wt. % (and all values and ranges therebetween) of the TiAlV alloy. At can be appreciated, the rhenium content in the above examples can be greater than the minimum amount to create the rhenium effect in the metal alloy.

In accordance with another and/or alternative non-limiting aspect of the present disclosure, there is provided a bone plate and/or fastener system that is formed of 50-100% (and all values and ranges therebetween) of a metal alloy that includes rhenium in a sufficient amount to create a rhenium effect in the metal alloy. In one non-limiting embodiment, the metal alloy includes at least 15 awt % rhenium, and at least 0.1 wt. % (e.g., 0.1-96 wt. % and all values and ranges therebetween) of one or more of aluminum, bismuth, chromium, cobalt, copper, hafnium, iridium, iron, magnesium, manganese, molybdenum, nickel, niobium, osmium, rhodium, ruthenium, silicon, silver, tantalum, technetium, titanium, tungsten, vanadium, yttrium, and zirconium.

In accordance with another and/or alternative non-limiting aspect of the present disclosure, there is provided a bone plate and/or fastener system that is formed of 50-100% (and all values and ranges therebetween) of a refractory metal alloy. The refractory metal alloy may or may not include sufficient rhenium to create a rhenium effect in the refractory metal alloy. As defined herein, a refractory metal alloy is a metal alloy that includes at least 20 wt. % of one or more of molybdenum, rhenium, niobium, tantalum, or tungsten. Non-limiting metal alloys include MoRe alloy, ReW alloy, MoReCr alloy, MoReTa alloy, MoReTi alloy, WCu alloy, ReCr, molybdenum alloy, rhenium alloy, tungsten alloy, tantalum alloy, niobium alloy, etc.

In accordance with another and/or alternative non-limiting aspect of the present disclosure, there is provided a bone plate and/or fastener system that is formed of 50-100% (and all values and ranges therebetween) of a metal alloy that includes rhenium in a sufficient amount to create a rhenium effect in the metal alloy, and the metal alloy is a standard stainless steel alloy that has been modified to include at least 15 awt. % rhenium.

In accordance with another and/or alternative non-limiting aspect of the present disclosure, there is provided a bone plate and/or fastener system that is formed of 50-100% (and all values and ranges therebetween) of a metal alloy that includes rhenium in a sufficient amount to create a rhenium effect in the metal alloy, and the metal alloy is a standard cobalt chromium alloy that has been modified to include at least 15 awt. % rhenium.

In accordance with another and/or alternative non-limiting aspect of the present disclosure, there is provided a bone plate and/or fastener system that is formed of 50-100% (and all values and ranges therebetween) of a metal alloy that includes rhenium in a sufficient amount to create a rhenium effect in the metal alloy, and the metal alloy is a standard TiAlV alloy that has been modified to include at least 15 awt. % rhenium.

Several non-limiting examples of the metal alloy in accordance with the present disclosure are set forth below in weight percent:

| Component/Wt. % | Ex. 1 | Ex. 2 | Ex. 3 | Ex. 4 |
|---|---|---|---|---|
| Ag | 0-40% | 0-40% | 0-40% | 0-40% |
| Al | 0-40% | 0-40% | 0-40% | 0-40% |
| Bi | 0-40% | 0-40% | 0-40% | 0-40% |
| Cr | 0-40% | 0-40% | 0-40% | 0-40% |
| Cu | 0-40% | 0-40% | 0-40% | 0-40% |
| Co | 0-60% | 0-60% | 0-60% | 0-60% |
| Fe | 0-80% | 0-80% | 0-80% | 0-80% |
| Hf | 0-40% | 0-40% | 0-40% | 0-40% |
| Ir | 0-40% | 0-40% | 0-40% | 0-40% |
| Mg | 0-40% | 0-40% | 0-40% | 0-40% |
| Mn | 0-40% | 0-40% | 0-40% | 0-40% |
| Mo | 0-98% | 0-95% | 0-95% | 0-95% |
| Nb | 0-80% | 0-80% | 0-80% | 0-80% |
| Ni | 0-60% | 0-60% | 0-60% | 0-60% |
| Os | 0-40% | 0-40% | 0-40% | 0-40% |
| Pt | 0-40% | 0-40% | 0-40% | 0-40% |
| Re | 0-98% | 0-90% | 0-80% | 0-70% |
| Rh | 0-40% | 0-40% | 0-40% | 0-40% |
| Si | 0-40% | 0-40% | 0-40% | 0-40% |
| Sn | 0-40% | 0-40% | 0-40% | 0-40% |
| Ta | 0-80% | 0-60% | 0-80% | 0-80% |
| Tc | 0-40% | 0-40% | 0-40% | 0-40% |
| Ti | 0-60% | 0-60% | 0-60% | 0-60% |
| V | 0-40% | 0-40% | 0-40% | 0-40% |
| W | 0-98% | 0-98% | 0-98% | 0-98% |
| Y | 0-40% | 0-40% | 0-40% | 0-40% |
| Zr | 0-40% | 0-40% | 0-40% | 0-40% |

| Component/Wt. % | Ex. 5 | Ex. 6 | Ex. 7 | Ex. 8 |
|---|---|---|---|---|
| Ag | 0-20% | 0-20% | 0-20% | 0-20% |
| Al | 0-35% | 0-30% | 0-30% | 0-25% |
| Bi | 0-20% | 0-20% | 0-20% | 0-20% |
| Cr | 0-40% | 0-40% | 0-40% | 0-40% |
| Cu | 0-20% | 0-20% | 0-20% | 0-20% |
| Co | 0-60% | 0-60% | 0-60% | 0-60% |
| Fe | 0-80% | 0-80% | 0-80% | 0-80% |
| Hf | 0-20% | 0-20% | 0-20% | 0-20% |
| Ir | 0-20% | 0-20% | 0-20% | 0-20% |
| Mg | 0-20% | 0-20% | 0-20% | 0-20% |
| Mn | 0-20% | 0-40% | 0-20% | 0-20% |
| Mo | 0-98% | 0-90% | 0-85% | 0-80% |
| Nb | 0-80% | 0-70% | 0-65% | 0-60% |
| Ni | 0-60% | 0-55% | 0-52% | 0-50% |
| Os | 0-20% | 0-20% | 0-20% | 0-20% |
| Pt | 0-20% | 0-20% | 0-20% | 0-20% |
| Re | 0-98% | 0-90% | 0-80% | 0-70% |
| Rh | 0-20% | 0-20% | 0-20% | 0-20% |
| Si | 0-20% | 0-20% | 0-20% | 0-20% |

-continued

| | | | | |
|---|---|---|---|---|
| Sn | 0-20% | 0-20% | 0-20% | 0-20% |
| Ta | 0-80% | 0-70% | 0-65% | 0-60% |
| Tc | 0-20% | 0-20% | 0-20% | 0-20% |
| Ti | 0-60% | 0-55% | 0-53% | 0-50% |
| V | 0-20% | 0-20% | 0-20% | 0-20% |
| W | 0-98% | 0-95% | 0-90% | 0-80% |
| Y | 0-20% | 0-20% | 0-20% | 0-20% |
| Zr | 0-20% | 0-20% | 0-20% | 0-20% |

| Component/Wt. % | Ex. 9 | Ex. 10 | Ex. 11 | Ex. 12 |
|---|---|---|---|---|
| Ag | 0-5% | 0-5% | 0-5% | 0-5% |
| Al | 0-5% | 0-5% | 1-15% | 0-20% |
| Bi | 0-5% | 0-5% | 0-5% | 0-5% |
| Cr | 1-28% | 1-30% | 0-5% | 0-30% |
| Cu | 0-20% | 0-5% | 0-5% | 0-25% |
| Co | 0-5% | 1-60% | 0-5% | 0-60% |
| Fe | 10-80% | 0-25% | 0-5% | 0-80% |
| Hf | 0-5% | 0-5% | 0-5% | 0-5% |
| Ir | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 0-8% | 0-25% | 0-5% | 0-98% |
| Nb | 0-5% | 0-5% | 0-5% | 0-95% |
| Ni | 1-20% | 1-45% | 0-5% | 0-5% |
| Os | 0-5% | 0-5% | 0-5% | 0-5% |
| Pt | 0-5% | 0-5% | 0-5% | 0-5% |
| Re | 5-20% | 4.8-20% | 4.5-20% | 4.5-20% |
| Rh | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 0-5% | 0-98% |
| Tc | 0-5% | 0-5% | 0-5% | 0-5% |
| Ti | 0-5% | 0-5% | 40-93% | 0-93% |
| V | 0-5% | 0-5% | 1-10% | 0-20% |
| W | 0-5% | 0-20% | 0-5% | 0-98% |
| Y | 0-5% | 0-5% | 0-5% | 0-5% |
| Zr | 0-5% | 0-5% | 0-5% | 0-5% |

| Component/Wt. % | Ex. 13 | Ex. 14 | Ex. 15 | Ex. 16 |
|---|---|---|---|---|
| Mo | 40-80% | 40-80% | 40-80% | 40-80% |
| C | 0.01-0.3% | 0-0.3% | 0-0.3% | 0-0.3% |
| Co | ≤0.002% | ≤0.002% | ≤0.002% | ≤0.002% |
| $Cs_2O$ | 0-0.2% | 0-0.2% | 0.01-0.2% | 0-0.2% |
| Fe | ≤0.02% | <0.02% | ≤0.02% | ≤0.02% |
| H | ≤0.002% | ≤0.002% | ≤0.002% | ≤0.002% |
| Hf | 0.1-2.5% | 0-2.5% | 0-2.5% | 0-2.5% |
| O | ≤0.06% | ≤0.06% | ≤0.06% | ≤0.06% |
| Os | ≤1% | <1% | ≤1% | ≤1% |
| $La_2O_3$ | 0-32% | 0.1-2% | 0-2% | 0-2% |
| N | ≤20 ppm | ≤20 ppm | ≤20 ppm | ≤20 ppm |
| Nb | ≤0.01% | ≤0.01% | ≤0.01% | ≤0.01% |
| Pt | ≤1% | ≤1% | ≤1% | ≤1% |
| R | 0-49% | 7.5-49% | 7.5-49% | 7.5-49% |
| S | ≤0.008% | ≤0.008% | ≤0.008% | ≤0.008% |
| Sn | ≤0.002% | <0.002% | ≤0.002% | ≤0.002% |
| Ta | 0-50% | 0-50% | 0-50% | 0-50% |
| Tc | ≤1% | ≤1% | ≤1% | ≤1% |
| Ti | ≤1% | ≤1% | ≤1% | ≤1% |
| V | ≤1% | <1% | ≤1% | ≤1% |
| W | 0-50% | 0-50% | 0-50% | 0.5-50% |
| $Y_2O_3$ | 0-1% | 0-1% | 0.1-1% | 0-1% |
| Zr | ≤1% | ≤1% | ≤1% | ≤1% |
| $ZrO_2$ | 0-3% | 0-3% | 0-3% | 0-3% |
| CNT | 0-10% | 0-10% | 0-10% | 0-10% |

| Component/Wt. % | Ex. 17 | Ex. 18 | Ex. 19 |
|---|---|---|---|
| Mo | 40-80% | 40-80% | 40-80% |
| C | 0-0.3% | 0-0.3% | 0-0.3% |
| Co | ≤0.002% | ≤0.002% | ≤0.002% |
| $Cs_2O$ | 0-0.2% | 0-0.2% | 0-0.2% |
| H | ≤0.002% | ≤0.002% | ≤0.002% |
| Hf | 0-2.5% | 0-2.5% | 0-2.5% |
| O | ≤0.06% | ≤0.06% | ≤0.06% |
| Os | ≤1% | ≤1% | ≤1% |
| $La_2O_3$ | 0-2% | 0-2% | 0-2% |
| N | ≤20 ppm | ≤20 ppm | ≤20 ppm |
| Nb | ≤0.01% | ≤0.01% | ≤0.01% |
| Pt | ≤1% | ≤1% | ≤1% |
| Re | 0-49% | 7.5-49% | 7.5-49% |
| S | ≤0.008% | ≤0.008% | ≤0.008% |
| Sn | ≤0.002% | ≤0.002% | ≤0.002% |
| Ta | 0-50% | 0.5-50% | 0-50% |
| Tc | ≤1% | ≤1% | ≤1% |
| Ti | ≤1% | ≤1% | ≤1% |
| V | ≤1% | ≤1% | ≤1% |
| W | 0-50% | 0-50% | 0-50% |
| $Y_2O_3$ | 0-1% | 0-1% | 0-1% |
| $ZrO_2$ | 0.1-3% | 0-3% | 0-3% |
| CNT | 0-10% | 0-10% | 0-10% |

| Component/Wt. % | Ex. 20 | Ex. 21 | Ex. 22 |
|---|---|---|---|
| Mo | 45-78% | 45-75% | 45-70% |
| C | 0-0.3% | 0-0.3% | 0-0.3% |
| Co | <0.002% | <0.002% | <0.002% |
| $Cs_2O$ | 0-0.2% | 0-0.2% | 0-0.2% |
| H | ≤0.002% | <0.002% | ≤0.002% |
| Hf | 0-2.5% | 0-2.5% | 0-2.5% |
| O | ≤0.06% | ≤0.06% | ≤0.06% |
| Os | ≤1% | ≤1% | ≤1% |
| $La_2O_3$ | 0-2% | 0-2% | 0-2% |
| N | ≤20 ppm | ≤20 ppm | ≤20 ppm |
| Nb | <0.01% | ≤0.01% | ≤0.01% |
| Pt | <1% | <1% | ≤1% |
| Re | 0-49% | 7.5-49% | 7.5-49% |
| S | ≤0.008% | ≤0.008% | ≤0.008% |
| Sn | ≤0.002% | ≤0.002% | ≤0.002% |
| Ta | 0-50% | 0.5-50% | 0-50% |
| Tc | ≤1% | ≤1% | ≤1% |
| Ti | ≤1% | ≤1% | ≤1% |
| V | ≤1% | ≤1% | ≤1% |
| W | 0-50% | 0-50% | 0-50% |
| $Y_2O_3$ | 0-1% | 0-1% | 0-1% |
| $ZrO_2$ | 0.1-3% | 0-3% | 0-3% |
| CNT | 0-10% | 0-10% | 0-10% |

| Component/Wt. % | Ex. 23 | Ex. 24 | Ex. 25 | Ex. 26 |
|---|---|---|---|---|
| Mo | 35-80% | 35-80% | 35-70% | 35-65% |
| C | 0.05-0.15% | 0-0.15% | 0-0.15% | 0-0.15% |
| $Cs_2O$ | 0-0.2% | 0-0.2% | 0.04-0.1% | 0-0.2% |
| Hf | 0.8-1.4% | 0-2% | 0-2.5% | 0-2.5% |
| $La_2O_3$ | 0-2% | 0.3-0.7% | 0-2% | 0-2% |
| Re | 0-49% | 7-49% | 7.5-49% | 7.5-49% |
| Ta | 0-2% | 0-2% | 0-50% | 0-50% |
| W | 0-2% | 0-2% | 0-50% | 20-50% |
| $Y_2O_3$ | 0-1% | 0-1% | 0.3-0.5% | 0-1% |
| $ZrO_2$ | 0-3% | 0-3% | 0-3% | 0-3% |

| Component/Wt. % | Ex. 27 | Ex. 28 | Ex. 29 |
|---|---|---|---|
| Mo | 40-60% | 35-60% | 30-60% |
| C | 0-0.15% | 0-0.15% | 0-0.15% |
| Cs2O | 0-0.2% | 0-0.2% | 0-0.2% |
| Hf | 0-2.5% | 0-2.5% | 0-2.5% |
| $La_2O_3$ | 0-2% | 0-2% | 0-2% |
| Re | 0-60% | 7.5-65% | 7.5-70% |
| Ta | 0-3% | 10-50% | 0-40% |
| W | 0-3% | 0-50% | 0-40% |
| $Y_2O_3$ | 0-1% | 0-1% | 0-1% |
| $ZrO_2$ | 1.2-1.8% | 0-3% | 0-3% |

| Component/Wt. % | Ex. 30 | Ex. 31 | Ex. 32 |
|---|---|---|---|
| W | 20-80% | 60-80% | 20-78% |
| Re | 0-47.5% | 10-40% | 8-47.5% |
| Mo | 0-47.5% | <0.5% | 1-47.5% |
| Cu | <0.5% | <0.5% | <0.5% |
| C | ≤0.15% | ≤0.15% | ≤0.15% |
| Co | ≤0.002% | ≤0.002% | ≤0.002% |
| $Cs_2O$ | ≤0.2% | ≤0.2% | ≤0.2% |
| Fe | <0.02% | ≤0.02% | ≤0.02% |
| H | ≤0.002% | ≤0.002% | ≤0.002% |
| Hf | <0.5% | <0.5% | <0.5% |
| $La_2O_3$ | <0.5% | <0.5% | <0.5% |

-continued

| | | | |
|---|---|---|---|
| O | ≤0.06% | ≤0.06% | ≤0.06% |
| Os | <0.5% | <0.5% | <0.5% |
| N | ≤20 ppm | ≤20 ppm | ≤20 ppm |
| Nb | ≤0.01% | <0.01% | ≤0.01% |
| Pt | <0.5% | <0.5% | <0.5% |
| S | <0.008% | <0.008% | ≤0.008% |
| Sn | <0.002% | ≤0.002% | ≤0.002% |
| Ta | <0.5% | <0.5% | <0.5% |
| Tc | <0.5% | <0.5% | <0.5% |
| Ti | <0.5% | <0.5% | <0.5% |
| V | <0.5% | <0.5% | <0.5% |
| $Y_2O_3$ | <0.5% | <0.5% | <0.5% |
| Zr | <0.5% | <0.5% | <0.5% |
| $ZrO_2$ | <0.5% | <0.5% | <0.5% |
| CNT | 0-10% | 0-10% | <0.5%. |

| Component/Wt. % | Ex. 33 | Ex. 34 | Ex. 35 |
|---|---|---|---|
| W | 20-80% | 60-80% | 20-75% |
| Re | 0-47.5% | 10-40% | 7.5-47.5% |
| Mo | 0-47.5% | <0.5% | 1-47.5% |

| Component/Wt. % | Ex. 36 | Ex. 37 | Ex. 38 |
|---|---|---|---|
| W | 50.1-80% | 65-80% | 50.1-79% |
| Re | 0-40% | 10-35% | 10-40% |
| Mo | 0-40% | <0.5% | 1-30% |

| Component/Wt. % | Ex. 39 | Ex. 40 | Ex. 41 |
|---|---|---|---|
| W | 20-49% | 20-49% | 20-49% |
| Re | 0-60% | 7.5-60% | 7.5-60% |
| Mo | 0-40% | 0-40% | 0-39% |

| Component/Wt. % | Ex. 42 | Ex. 43 | Ex. 44 |
|---|---|---|---|
| Re | 5-98% | 60-95% | 80-90% |
| Mo | 0-80% | 0-40% | 0-20% |
| W | 0-80% | 0-40% | 0-20% |

| Component/Wt. % | Ex. 45 | Ex. 46 | Ex. 47 |
|---|---|---|---|
| W | 20-49% | 20-49% | 20-49% |
| Re | 0-40% | 6-40% | 6-39% |
| Mo | 20-60% | 30-60% | 40-60% |

| Component/Wt. % | Ex. 48 | Ex. 49 | Ex. 50 |
|---|---|---|---|
| W | 20-40% | 20-35% | 20-30% |
| Re | 0-40% | 6-40% | 6-40% |
| Mo | 0-40% | 10-40% | 31-40% |

| Component/Wt. % | Ex. 51 | Ex. 52 | Ex. 53 | Ex. 54 |
|---|---|---|---|---|
| Re | 5-60% | 5-60% | 5-60% | 5-60% |
| Mo | 0-55% | 10-55% | 10-55% | 10-55% |
| Bi | 1-42 | 0-32 | 0-32 | 0-32 |
| Cr | 0-32 | 1-42 | 0-32 | 0-32 |
| Ir | 0-32 | 0-32 | 1-42 | 0-32 |
| Nb | 0-32 | 0-32 | 0-32 | 1-42 |
| Ta | 0-32 | 0-32 | 0-32 | 0-32 |
| Ti | 0-32 | 0-32 | 0-32 | 0-32 |
| Y | 0-32 | 0-32 | 0-32 | 0-32 |
| Zr | 0-32 | 0-32 | 0-32 | 0-32 |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/Wt. % | Ex. 55 | Ex. 56 | Ex. 57 | Ex. 58 |
|---|---|---|---|---|
| Re | 5-60% | 5-60% | 5-60% | 5-60% |
| Mo | 15-55% | 15-55% | 15-55% | 15-55% |
| Bi | 0-32 | 0-32 | 0-32 | 0-32 |
| Cr | 0-32 | 0-32 | 0-32 | 0-32 |
| Ir | 0-32 | 0-32 | 0-32 | 0-32 |
| Nb | 0-32 | 0-32 | 0-32 | 0-32 |
| Ta | 1-42 | 0-32 | 0-32 | 0-32 |
| Ti | 0-32 | 1-42 | 0-32 | 0-32 |
| Y | 0-32 | 0-32 | 1-42 | 0-32 |
| Zr | 0-32 | 0-32 | 0-32 | 1-42 |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/Wt. % | Ex. 59 | Ex. 60 | Ex. 61 | Ex. 62 |
|---|---|---|---|---|
| Re | 41-59% | 41-59% | 41-59% | 41-59% |
| Mo | 18-45% | 18-45% | 18-45% | 18-45% |
| Bi | 1-42 | 0-32 | 0-32 | 0-32 |
| Cr | 0-32 | 1-42 | 0-32 | 0-32 |
| Ir | 0-32 | 0-32 | 1-42 | 0-32 |
| Nb | 0-32 | 0-32 | 0-32 | 1-42 |
| Ta | 0-32 | 0-32 | 0-32 | 0-32 |
| Ti | 0-32 | 0-32 | 0-32 | 0-32 |
| Y | 0-32 | 0-32 | 0-32 | 0-32 |
| Zr | 0-32 | 0-32 | 0-32 | 0-32 |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/Wt. % | Ex. 63 | Ex. 64 | Ex. 65 | Ex. 66 |
|---|---|---|---|---|
| Re | 41-59% | 41-59% | 41-59% | 41-59% |
| Mo | 18-45% | 18-45% | 18-45% | 18-45% |
| Bi | 0-32 | 0-32 | 0-32 | 0-32 |
| Cr | 0-32 | 0-32 | 0-32 | 0-32 |
| Ir | 0-32 | 0-32 | 0-32 | 0-32 |
| Nb | 0-32 | 0-32 | 0-32 | 0-32 |
| Ta | 1-42 | 0-32 | 0-32 | 0-32 |
| Ti | 0-32 | 1-42 | 0-32 | 0-32 |
| Y | 0-32 | 0-32 | 1-42 | 0-32 |
| Zr | 0-32 | 0-32 | 0-32 | 1-42 |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/Wt. % | Ex. 67 | Ex. 68 | Ex. 69 | Ex. 70 |
|---|---|---|---|---|
| Re | 41-59% | 41-59% | 41-59% | 41-59% |
| Mo | 18-45% | 18-45% | 18-45% | 18-45% |
| Bi | 0-15 | 0-15 | 1-36 | 0-15 |
| Cr | 1-20 | 1-20 | 1-20 | 1-20 |
| Ir | 0-15 | 0-15 | 0-15 | 0-15 |
| Nb | 1-36 | 0-15 | 0-15 | 0-15 |
| Ta | 0-15 | 1-36 | 0-15 | 0-15 |
| Ti | 0-15 | 0-15 | 0-15 | 0-15 |
| Y | 0-15 | 0-15 | 0-15 | 0-15 |
| Zr | 0-15 | 0-15 | 0-15 | 1-36 |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/Wt. % | Ex. 71 | Ex. 72 | Ex. 73 | Ex. 74 |
|---|---|---|---|---|
| Re | 41-59% | 41-59% | 41-59% | 41-59% |
| Mo | 18-45% | 18-45% | 18-45% | 18-45% |
| Bi | 1-36 | 0-15 | 0-15 | 0-15 |
| Cr | 1-20 | 1-20 | 1-20 | 1-20 |
| Ir | 0-15 | 1-36 | 0-15 | 0-15 |
| Nb | 0-15 | 0-15 | 0-15 | 0-15 |
| Ta | 0-15 | 0-15 | 0-15 | 0-15 |
| Ti | 0-15 | 0-15 | 1-36 | 0-15 |
| Y | 0-15 | 0-15 | 0-15 | 1-36 |
| Zr | 0-15 | 0-15 | 0-15 | 0-15 |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/Wt. % | Ex. 75 | Ex. 76 | Ex. 77 | Ex. 78 |
|---|---|---|---|---|
| Re | 41-59% | 41-59% | 41-59% | 41-59% |
| Mo | 18-45% | 18-45% | 18-45% | 18-45% |
| B | 1-34 | 0-15 | 0-15 | 0-15 |
| Cr | 0-15 | 0-15 | 0-15 | 0-15 |
| Ir | 0-15 | 0-15 | 0-15 | 1-34 |
| Nb | 3-27 | 3-27 | 3-27 | 3-27 |
| Ta | 0-42 | 1-34 | 0-15 | 0-15 |
| Ti | 0-15 | 0-15 | 0-15 | 0-15 |

-continued

| | | | | |
|---|---|---|---|---|
| Y | 0-15 | 0-15 | 0-15 | 0-15 |
| Zr | 0-15 | 0-15 | 3-27 | 0-15 |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/Wt. % | Ex. 79 | Ex. 80 | Ex. 81 | Ex. 82 |
|---|---|---|---|---|
| Re | 41-59% | 41-59% | 41-59% | 41-59% |
| Mo | 18-45% | 18-45% | 18-45% | 18-45% |
| Bi | 0-15 | 0-15 | 0-15 | 0-15 |
| Cr | 0-15 | 0-15 | 0-15 | 0-15 |
| Ir | 0-15 | 1-34 | 0-15 | 0-15 |
| Nb | 0-15 | 0-15 | 0-15 | 0-15 |
| T | 1-34 | 0-15 | 3-27 | 0-15 |
| Ti | 0-15 | 0-15 | 0-15 | 0-15 |
| Y | 0-15 | 0-15 | 0-15 | 3-27 |
| Zr | 3-27 | 3-27 | 3-27 | 3-27 |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/Wt. % | Ex. 83 | Ex. 84 | Ex. 85 | Ex. 86 |
|---|---|---|---|---|
| Re | 41-59% | 41-59% | 41-59% | 41-59% |
| Mo | 18-45% | 18-45% | 18-45% | 18-45% |
| Bi | 0-15 | 0-15 | 0-15 | 0-15 |
| Cr | 0-15 | 0-15 | 0-15 | 1-10 |
| Ir | 1-34 | 0-25 | 3-27 | 0-15 |
| Nb | 0-15 | 3-27 | 0-15 | 0-15 |
| Ta | 0-15 | 0-15 | 1-34 | 0-15 |
| Ti | 0-15 | 0-15 | 0-15 | 0-15 |
| Y | 3-27 | 3-27 | 0-15 | 0-15 |
| Zr | 0-15 | 0-15 | 3-27 | 1-12 |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/Wt. % | Ex. 87 | Ex. 88 | Ex. 89 | Ex. 90 |
|---|---|---|---|---|
| Re | 50-75% | 55-75% | 60-75% | 65-75% |
| Cr | 25-50% | 25-45% | 25-40% | 25-35% |
| Mo | 0-25% | 0-25% | 0-25% | 0-25% |
| Bi | 0-25% | 0-25% | 0-25% | 0-25% |
| Cr | 0-25% | 0-25% | 0-25% | 0-25% |
| Ir | 0-25% | 0-25% | 0-25% | 0-25% |
| Nb | 0-25% | 0-25% | 0-25% | 0-25% |
| Ta | 0-25% | 0-25% | 0-25% | 0-25% |
| V | 0-25% | 0-25% | 0-25% | 0-25% |
| W | 0-25% | 0-25% | 0-25% | 0-25% |
| Mn | 0-25% | 0-25% | 0-25% | 0-25% |
| Tc | 0-25% | 0-25% | 0-25% | 0-25% |
| Ru | 0-25% | 0-25% | 0-25% | 0-25% |
| Rh | 0-25% | 0-25% | 0-25% | 0-25% |
| Hf | 0-25% | 0-25% | 0-25% | 0-25% |
| Os | 0-25% | 0-25% | 0-25% | 0-25% |
| Cu | 0-25% | 0-25% | 0-25% | 0-25% |
| Ir | 0-25% | 0-25% | 0-25% | 0-25% |
| Ti | 0-25% | 0-25% | 0-25% | 0-25% |
| Y | 0-25% | 0-25% | 0-25% | 0-25% |
| Zr | 0-25% | 0-25% | 0-25% | 0-25% |
| Ag | 0-25% | 0-25% | 0-25% | 0-25% |
| Al | 0-25% | 0-25% | 0-25% | 0-25% |
| Co | 0-25% | 0-25% | 0-25% | 0-25% |
| Fe | 0-25% | 0-25% | 0-25% | 0-25% |
| Mg | 0-25% | 0-25% | 0-25% | 0-25% |
| Ni | 0-25% | 0-25% | 0-25% | 0-25% |
| Pt | 0-25% | 0-25% | 0-25% | 0-25% |
| Si | 0-25% | 0-25% | 0-25% | 0-25% |
| S | 0-25% | 0-25% | 0-25% | 0-25% |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/Wt. % | Ex. 91 | Ex. 92 | Ex. 93 | Ex. 94 |
|---|---|---|---|---|
| Re | 50-72% | 55-72% | 60-72% | 65-72% |
| Cr | 28-50% | 28-45% | 28-40% | 28-35% |
| Mo | 0-25% | 0-25% | 0-25% | 0-25% |
| Bi | 0-10% | 0-10% | 0-10% | 0-10% |
| Cr | 0-10% | 0-10% | 0-10% | 0-10% |
| Ir | 0-10% | 0-10% | 0-10% | 0-10% |
| Nb | 0-10% | 0-10% | 0-10% | 0-10% |
| Ta | 0-10% | 0-10% | 0-10% | 0-10% |
| V | 0-10% | 0-10% | 0-10% | 0-10% |
| W | 0-10% | 0-10% | 0-10% | 0-10% |
| Mn | 0-10% | 0-10% | 0-10% | 0-10% |
| Tc | 0-10% | 0-10% | 0-10% | 0-10% |
| Ru | 0-10% | 0-10% | 0-10% | 0-10% |
| Rh | 0-10% | 0-10% | 0-10% | 0-10% |
| Hf | 0-10% | 0-10% | 0-10% | 0-10% |
| Os | 0-10% | 0-10% | 0-10% | 0-10% |
| Cu | 0-10% | 0-10% | 0-10% | 0-10% |
| Ir | 0-10% | 0-10% | 0-10% | 0-10% |
| Ti | 0-10% | 0-10% | 0-10% | 0-10% |
| Y | 0-10% | 0-10% | 0-10% | 0-10% |
| Zr | 0-10% | 0-10% | 0-10% | 0-10% |
| Ag | 0-10% | 0-10% | 0-10% | 0-10% |
| Al | 0-10% | 0-10% | 0-10% | 0-10% |
| Co | 0-10% | 0-10% | 0-10% | 0-10% |
| Fe | 0-10% | 0-10% | 0-10% | 0-10% |
| Mg | 0-10% | 0-10% | 0-10% | 0-10% |
| Ni | 0-10% | 0-10% | 0-10% | 0-10% |
| Pt | 0-10% | 0-10% | 0-10% | 0-10% |
| Si | 0-10% | 0-10% | 0-10% | 0-10% |
| Sn | 0-10% | 0-10% | 0-10% | 0-10% |
| C | <0.06 | <0.06 | <0.06 | <0.06 |
| N | <0.06 | <0.06 | <0.06 | <0.06 |
| O | <0.06 | <0.06 | <0.06 | <0.06 |

-continued

| Component/Wt. % | Ex. 95 | Ex. 96 | Ex. 97 | Ex. 98 |
|---|---|---|---|---|
| Re | 50-70% | 55-70% | 60-70% | 65-70% |
| Cr | 30-50% | 30-45% | 30-40% | 30-35% |
| Mo | 0-10% | 0-10% | 0-10% | 0-10% |
| Bi | 0-10% | 0-10% | 0-10% | 0-10% |
| Cr | 0-10% | 0-10% | 0-10% | 0-10% |
| Ir | 0-10% | 0-10% | 0-10% | 0-10% |
| Nb | 0-10% | 0-10% | 0-10% | 0-10% |
| Ta | 0-10% | 0-10% | 0-10% | 0-10% |
| V | 0-10% | 0-10% | 0-10% | 0-10% |
| W | 0-10% | 0-10% | 0-10% | 0-10% |
| Mn | 0-10% | 0-10% | 0-10% | 0-10% |
| Tc | 0-10% | 0-10% | 0-10% | 0-10% |
| Ru | 0-10% | 0-10% | 0-10% | 0-10% |
| Rh | 0-10% | 0-10% | 0-10% | 0-10% |
| Hf | 0-10% | 0-10% | 0-10% | 0-10% |
| Os | 0-10% | 0-10% | 0-10% | 0-10% |
| Cu | 0-10% | 0-10% | 0-10% | 0-10% |
| Ir | 0-10% | 0-10% | 0-10% | 0-10% |
| Ti | 0-10% | 0-10% | 0-10% | 0-10% |
| Y | 0-10% | 0-10% | 0-10% | 0-10% |
| Zr | 0-10% | 0-10% | 0-10% | 0-10% |
| Ag | 0-10% | 0-10% | 0-10% | 0-10% |
| Al | 0-10% | 0-10% | 0-10% | 0-10% |
| Co | 0-10% | 0-10% | 0-10% | 0-10% |
| Fe | 0-10% | 0-10% | 0-10% | 0-10% |
| Mg | 0-10% | 0-10% | 0-10% | 0-10% |
| Ni | 0-10% | 0-10% | 0-10% | 0-10% |
| Pt | 0-10% | 0-10% | 0-10% | 0-10% |
| Si | 0-10% | 0-10% | 0-10% | 0-10% |
| Sn | 0-10% | 0-10% | 0-10% | 0-10% |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/Wt. % | Ex. 99 | Ex. 100 | Ex. 101 | Ex. 102 |
|---|---|---|---|---|
| Re | 50-67.5% | 55-67.5% | 60-67.5% | 65-67.5% |
| Cr | 32.5-50% | 32.5-45% | 32.5-40% | 32.5-35% |
| Mo | 0-10% | 0-10% | 0-10% | 0-10% |
| Bi | 0-10% | 0-10% | 0-10% | 0-10% |
| Cr | 0-10% | 0-10% | 0-10% | 0-10% |
| Ir | 0-10% | 0-10% | 0-10% | 0-10% |
| Nb | 0-10% | 0-10% | 0-10% | 0-10% |
| Ta | 0-10% | 0-10% | 0-10% | 0-10% |
| V | 0-10% | 0-10% | 0-10% | 0-10% |
| W | 0-10% | 0-10% | 0-10% | 0-10% |

-continued

| | | | | |
|---|---|---|---|---|
| Mn | 0-10% | 0-10% | 0-10% | 0-10% |
| Tc | 0-10% | 0-10% | 0-10% | 0-10% |
| Ru | 0-10% | 0-10% | 0-10% | 0-10% |
| Rh | 0-10% | 0-10% | 0-10% | 0-10% |
| Hf | 0-10% | 0-10% | 0-10% | 0-10% |
| Os | 0-10% | 0-10% | 0-10% | 0-10% |
| Cu | 0-10% | 0-10% | 0-10% | 0-10% |
| Ir | 0-10% | 0-10% | 0-10% | 0-10% |
| Ti | 0-10% | 0-10% | 0-10% | 0-10% |
| Y | 0-10% | 0-10% | 0-10% | 0-10% |
| Zr | 0-10% | 0-10% | 0-10% | 0-10% |
| Ag | 0-10% | 0-10% | 0-10% | 0-10% |
| Al | 0-10% | 0-10% | 0-10% | 0-10% |
| Co | 0-10% | 0-10% | 0-10% | 0-10% |
| Fe | 0-10% | 0-10% | 0-10% | 0-10% |
| Mg | 0-10% | 0-10% | 0-10% | 0-10% |
| Ni | 0-10% | 0-10% | 0-10% | 0-10% |
| Pt | 0-10% | 0-10% | 0-10% | 0-10% |
| Si | 0-10% | 0-10% | 0-10% | 0-10% |
| Sn | 0-10% | 0-10% | 0-10% | 0-10% |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/Wt. % | Ex. 103 | Ex. 104 | Ex. 105 | Ex. 106 |
|---|---|---|---|---|
| Re | 50-67.5% | 55-67.5% | 60-67.5% | 65-67.5% |
| Cr | 32.5-50% | 32.5-45% | 32.5-40% | 32.5-35% |
| Mo | 0-5% | 0-5% | 0-5% | 0-5% |
| Bi | 0-5% | 0-5% | 0-5% | 0-5% |
| Cr | 0-5% | 0-5% | 0-5% | 0-5% |
| Ir | 0-5% | 0-5% | 0-5% | 0-5% |
| Nb | 0-5% | 0-5% | 0-5% | 0-5% |
| Ta | 0-5% | 0-5% | 0-5% | 0-5% |
| V | 0-5% | 0-5% | 0-5% | 0-5% |
| w | 0-5% | 0-5% | 0-5% | 0-5% |
| Mn | 0-5% | 0-5% | 0-5% | 0-5% |
| Tc | 0-5% | 0-5% | 0-5% | 0-5% |
| Ru | 0-5% | 0-5% | 0-5% | 0-5% |
| Rh | 0-5% | 0-5% | 0-5% | 0-5% |
| Hf | 0-5% | 0-5% | 0-5% | 0-5% |
| Os | 0-5% | 0-5% | 0-5% | 0-5% |
| Cu | 0-5% | 0-5% | 0-5% | 0-5% |
| Ir | 0-5% | 0-5% | 0-5% | 0-5% |
| Ti | 0-5% | 0-5% | 0-5% | 0-5% |
| Y | 0-5% | 0-5% | 0-5% | 0-5% |
| Zr | 0-5% | 0-5% | 0-5% | 0-5% |
| Ag | 0-5% | 0-5% | 0-5% | 0-5% |
| Al | 0-5% | 0-5% | 0-5% | 0-5% |
| Co | 0-5% | 0-5% | 0-5% | 0-5% |
| Fe | 0-5% | 0-5% | 0-5% | 0-5% |
| Mg | 0-5% | 0-5% | 0-5% | 0-5% |
| Ni | 0-5% | 0-5% | 0-5% | 0-5% |
| Pt | 0-5% | 0-5% | 0-5% | 0-5% |
| Si | 0-5% | 0-5% | 0-5% | 0-5% |
| Sn | 0-5% | 0-5% | 0-5% | 0-5% |
| C | <0.06 | <0.06 | <0.06 | <0.06 |
| N | <0.06 | <0.06 | <0.06 | <0.06 |
| O | <0.06 | <0.06 | <0.06 | <0.06 |

| Component/Wt. % | Ex. 107 | Ex. 108 | Ex. 109 | Ex. 110 |
|---|---|---|---|---|
| Mo | 40-95% | 40-95% | 40-95% | 40-95% |
| C | 0.01-0.3% | 0-0.3% | 0-0.3% | 0-0.3% |
| Co | <0.002% | ≤0.002% | ≤0.002% | ≤0.002% |
| $Cs_2O$ | 0-0.2% | 0-0.2% | 0.01-0.2% | 0-0.2% |
| Fe | ≤0.02% | ≤0.02% | ≤0.02% | ≤0.02% |
| H | <0.002% | <0.002% | ≤0.002% | ≤0.002% |
| Hf | 0.1-2.5% | 0-2.5% | 0-2.5% | 0-2.5% |
| 0 | ≤0.06% | ≤0.06% | ≤0.06% | ≤0.06% |
| Os | ≤1% | ≤1% | ≤1% | ≤1% |
| $La_2O_3$ | 0-2% | 0.1-2% | 0-2% | 0-2% |
| N | ≤20 ppm | ≤20 ppm | ≤20 ppm | ≤20 ppm |
| Nb | ≤0.01% | ≤0.01% | <0.01% | ≤0.01% |
| Pt | ≤1% | ≤1% | ≤1% | ≤1% |
| Re | 0-40% | 5-40% | 5-40% | 5-40% |
| S | ≤0.008% | ≤0.008% | ≤0.008% | ≤0.008% |
| Sn | <0.002% | <0.002% | ≤0.002% | ≤0.002% |
| Ta | 0-50% | 0-50% | 0-50% | 0-50% |

-continued

| | | | | |
|---|---|---|---|---|
| Tc | <1% | ≤1% | ≤1% | ≤1% |
| Ti | ≤1% | ≤1% | ≤1% | ≤1% |
| V | ≤1% | ≤1% | ≤1% | ≤1% |
| W | 0-50% | 0-50% | 0-50% | 0.5-50% |
| $Y_2O_3$ | 0-1% | 0-1% | 0.1-1% | 0-1% |
| Zr | ≤1% | ≤1% | ≤1% | ≤1% |
| $ZrO_2$ | 0-3% | 0-3% | 0-3% | 0-3% |
| Ag | 0-5% | 0-5% | 0-5% | 0-5% |
| Al | 0-5% | 0-5% | 0-5% | 0-5% |
| Co | 0-5% | 0-5% | 0-5% | 0-5% |
| Mg | 0-5% | 0-5% | 0-5% | 0-5% |
| Ni | 0-5% | 0-5% | 0-5% | 0-5% |
| Si | 0-5% | 0-5% | 0-5% | 0-5% |
| Sn | 0-5% | 0-5% | 0-5% | 0-5% |
| CNT | 0-10% | 0-10% | 0-10% | 0-10% |

| Component/Wt. % | Ex. 111 | Ex. 112 | Ex. 113 |
|---|---|---|---|
| Mo | 40-95% | 40-95% | 40-95% |
| C | 0-0.3% | 0-0.3% | 0-0.3% |
| Co | ≤0.002% | ≤0.002% | ≤0.002% |
| $Cs_2O$ | 0-0.2% | 0-0.2% | 0-0.2% |
| H | ≤0.002% | ≤0.002% | ≤0.002% |
| Hf | 0-2.5% | 0-2.5% | 0-2.5% |
| O | ≤0.06% | ≤0.06% | ≤0.06% |
| Os | ≤1% | <1% | ≤1% |
| $La_2O_3$ | 0-2% | 0-2% | 0-2% |
| N | ≤20 ppm | ≤20 ppm | ≤20 ppm |
| Nb | <0.01% | ≤0.01% | ≤0.01% |
| Pt | ≤1% | ≤1% | ≤1% |
| Re | 0-40% | 5-40% | 5-40% |
| S | ≤0.008% | ≤0.008% | ≤0.008% |
| Sn | ≤0.002% | ≤0.002% | ≤0.002% |
| Ta | 0-50% | 0.5-50% | 0-50% |
| Tc | ≤1% | <1% | ≤1% |
| Ti | ≤1% | ≤1% | ≤1% |
| V | <1% | ≤1% | ≤1% |
| W | 0-50% | 0-50% | 0-50% |
| $Y_2O_3$ | 0-1% | 0-1% | 0-1% |
| $ZrO_2$ | 0.1-3% | 0-3% | 0-3% |
| Ag | 0-5% | 0-5% | 0-5% |
| Al | 0-5% | 0-5% | 0-5% |
| Fe | 0-5% | 0-5% | 0-5% |
| Mg | 0-5% | 0-5% | 0-5% |
| Ni | 0-5% | 0-5% | 0-5% |
| Si | 0-5% | 0-5% | 0-5% |
| CNT | 0-10% | 0-10% | 0-10% |

| Component/Wt. % | Ex. 114 | Ex. 115 | Ex. 116 |
|---|---|---|---|
| Mo | 60-95% | 60-95% | 60-90% |
| C | 0-0.3% | 0-0.3% | 0-0.3% |
| Co | ≤0.002% | ≤0.002% | ≤0.002% |
| $Cs_2O$ | 0-0.2% | 0-0.2% | 0-0.2% |
| H | ≤0.002% | ≤0.002% | <0.002% |
| Hf | 0-2.5% | 0-2.5% | 0-2.5% |
| O | ≤0.06% | ≤0.06% | ≤0.06% |
| Os | ≤1% | ≤1% | ≤1% |
| $La_2O_3$ | 0-2% | 0-2% | 0-2% |
| N | ≤20 ppm | ≤20 ppm | ≤20 ppm |
| Nb | ≤0.01% | <0.01% | ≤0.01% |
| Pt | ≤1% | ≤1% | ≤1% |
| Re | 0-40% | 5-40% | 10-40% |
| S | ≤0.008% | <0.008% | ≤0.008% |
| Sn | <0.002% | ≤0.002% | ≤0.002% |
| Ta | 0-50% | 0.5-50% | 0-50% |
| Tc | ≤1% | ≤1% | ≤1% |
| Ti | ≤1% | ≤1% | ≤1% |
| V | ≤1% | ≤1% | ≤1% |
| W | 0-50% | 0-50% | 0-50% |
| $Y_2O_3$ | 0-1% | 0-1% | 0-1% |
| $ZrO_2$ | 0.1-3% | 0-3% | 0-3% |
| Ag | 0-5% | 0-5% | 0-5% |
| Al | 0-5% | 0-5% | 0-5% |
| Fe | 0-5% | 0-5% | 0-5% |
| Mg | 0-5% | 0-5% | 0-5% |

-continued

| | | | |
|---|---|---|---|
| Ni | 0-5% | 0-5% | 0-5% |
| Si | 0-5% | 0-5% | 0-5% |
| CNT | 0-10% | 0-10% | 0-10% |

| Component/Wt. % | Ex. 117 | Ex. 118 | Ex. 119 | Ex. 120 |
|---|---|---|---|---|
| Mo | 60-95% | 60-95% | 50-95% | 40-80% |
| C | 0.05-0.15% | 0-0.15% | 0-0.15% | 0-0.15% |
| $Cs_2O$ | 0-0.2% | 0-0.2% | 0.04-0.1% | 0-0.2% |
| Hf | 0.8-1.4% | 0-2% | 0-2.5% | 0-2.5% |
| $La_2O_3$ | 0-2% | 0.3-0.7% | 0-2% | 0-2% |
| Re | 0-40% | 5-40% | 5-40% | 5-40% |
| Ta | 0-2% | 0-2% | 0-50% | 0-50% |
| W | 0-2% | 0-2% | 0-50% | 20-50% |
| $Y_2O_3$ | 0-1% | 0-1% | 0.3-0.5% | 0-1% |
| $ZrO_2$ | 0-3% | 0-3% | 0-3% | 0-3% |

| Component/Wt. % | Ex. 121 | Ex. 122 | Ex. 123 |
|---|---|---|---|
| Mo | 97-95% | 50-90% | 60-95% |
| C | 0-0.15% | 0-0.15% | 0-0.15% |
| Cs2O | 0-0.2% | 0-0.2% | 0-0.2% |
| Hf | 0-2.5% | 0-2.5% | 0-2.5% |
| $La_2O_3$ | 0-2% | 0-2% | 0-2% |
| Re | 0-30 | 5-40% | 5-40% |
| Ta | 0-3% | 10-50% | 0-40% |
| W | 0-3% | 0-50% | 0-40% |
| $Y_2O_3$ | 0-1% | 0-1% | 0-1% |
| $ZrO_2$ | 1.2-1.8% | 0-3% | 0-3% |

| Component/Wt. % | Ex. 124 | Ex. 125 | Ex. 126 |
|---|---|---|---|
| W | 20-95% | 60-95% | 20-80% |
| Re | 0-47.5% | 5-40% | 5-47.5% |
| Mo | 0-47.5% | <0.5% | 1-47.5% |
| Cu | <0.5% | <0.5% | <0.5% |
| C | <0.15% | ≤0.15% | ≤0.15% |
| Co | ≤0.002% | ≤0.002% | ≤0.002% |
| $Cs_2O$ | <0.2% | <0.2% | ≤0.2% |
| Fe | <0.02% | ≤0.02% | ≤0.02% |
| H | ≤0.002% | ≤0.002% | ≤0.002% |
| Hf | <0.5% | <0.5% | <0.5% |
| $La_2O_3$ | <0.5% | <0.5% | <0.5% |
| 0 | ≤0.06% | ≤0.06% | ≤0.06% |
| Os | <0.5% | <0.5% | <0.5% |
| N | ≤20 ppm | ≤20 ppm | ≤20 ppm |
| Nb | ≤0.01% | <0.01% | ≤0.01% |
| Pt | <0.5% | <0.5% | <0.5% |
| S | ≤0.008% | ≤0.008% | ≤0.008% |
| Sn | ≤0.002% | ≤0.002% | ≤0.002% |
| Ta | <0.5% | <0.5% | <0.5% |
| Tc | <0.5% | <0.5% | <0.5% |
| Ti | <0.5% | <0.5% | <0.5% |
| V | <0.5% | <0.5% | <0.5% |
| $Y_2O_3$ | <0.5% | <0.5% | <0.5% |
| Zr | <0.5% | <0.5% | <0.5% |
| $ZrO_2$ | <0.5% | <0.5% | <0.5% |
| Ag | 0-5% | 0-5% | 0-5% |
| Al | 0-5% | 0-5% | 0-5% |
| Fe | 0-5% | 0-5% | 0-5% |
| Mg | 0-5% | 0-5% | 0-5% |
| Ni | 0-5% | 0-5% | 0-5% |
| Si | 0-5% | 0-5% | 0-5% |
| CNT | 0-10% | 0-10% | <0.5%. |

| Component/Wt. % | Ex. 127 | Ex. 128 | Ex. 129 | Ex. 130 |
|---|---|---|---|---|
| W | 1-94.9% | 1-94.9% | 1-94.9% | 10-95% |
| Cu | 0.1-94% | 0.1-94% | 0.1-94% | 1-84% |
| C | 0.01-0.3% | 0-0.3% | 0-0.3% | 0-0.3% |
| Co | ≤0.002% | ≤0.002% | ≤0.002% | ≤0.002% |
| $Cs_2O$ | 0-0.2% | 0-0.2% | 0.01-0.2% | 0-0.2% |
| Fe | ≤0.02% | ≤0.02% | ≤0.02% | ≤0.02% |
| H | ≤0.002% | ≤0.002% | ≤0.002% | ≤0.002% |
| Hf | 0.1-2.5% | 0-2.5% | 0-2.5% | 0-2.5% |
| O | <0.06% | ≤0.06% | ≤0.06% | ≤0.06% |
| Os | ≤1% | ≤1% | ≤1% | ≤1% |
| $La_2O_3$ | 0-2% | 0.1-2% | 0-2% | 0-2% |
| Mo | 0-5% | 0.1-3% | 0-2% | 0-3% |
| N | ≤20 ppm | ≤20 ppm | ≤20 ppm | ≤20 ppm |
| Nb | ≤0.01% | ≤0.01% | ≤0.01% | ≤0.01% |
| Pt | ≤1% | ≤1% | ≤1% | ≤1% |
| Re | 0-40% | 5-40% | 5-40% | 6-40% |
| S | ≤0.008% | <0.008% | ≤0.008% | ≤0.008% |
| Sn | ≤0.002% | ≤0.002% | <0.002% | ≤0.002% |
| Ta | 0-50% | 0-50% | 0-50% | 0-50% |
| Tc | ≤1% | ≤1% | ≤1% | ≤1% |
| Ti | ≤1% | ≤1% | ≤1% | ≤1% |
| V | <1% | ≤1% | ≤1% | ≤1% |
| $Y_2O_3$ | 0-1% | 0-1% | 0.1-1% | 0-1% |
| Zr | ≤1% | ≤1% | ≤1% | ≤1% |
| $ZrO_2$ | 0-3% | 0-3% | 0-3% | 0-3% |
| Ag | 0-5% | 0-5% | 0-5% | 0-5% |
| Al | 0-5% | 0-5% | 0-5% | 0-5% |
| Fe | 0-5% | 0-5% | 0-5% | 0-5% |
| Mg | 0-5% | 0-5% | 0-5% | 0-5% |
| Ni | 0-5% | 0-5% | 0-5% | 0-5% |
| Si | 0-5% | 0-5% | 0-5% | 0-5% |
| CNT | 0-10% | 0-10% | 0-10% | 0-10% |

| Component/Wt. % | Ex. 131 | Ex. 132 | Ex. 133 |
|---|---|---|---|
| W | 20-96% | 25-92% | 30-88% |
| Cu | 2-74% | 2-68% | 5-62% |
| C | 0-0.3% | 0-0.3% | 0-0.3% |
| Co | ≤0.002% | ≤0.002% | ≤0.002% |
| $Cs_2O$ | 0-0.2% | 0-0.2% | 0-0.2% |
| H | ≤0.002% | ≤0.002% | ≤0.002% |
| Hf | 0-2.5% | 0-2.5% | 0-2.5% |
| O | ≤0.06% | ≤0.06% | ≤0.06% |
| Os | ≤1% | ≤1% | ≤1% |
| $La_2O_3$ | 0-2% | 0-2% | 0-2% |
| Mo | 0-3% | 0-2% | 0-1% |
| N | ≤20 ppm | ≤20 ppm | ≤20 ppm |
| Nb | ≤0.01% | ≤0.01% | <0.01% |
| Pt | ≤1% | ≤1% | ≤1% |
| Re | 0-40% | 7-40% | 8-40% |
| S | ≤0.008% | ≤0.008% | ≤0.008% |
| Sn | ≤0.002% | ≤0.002% | ≤0.002% |
| Ta | 0-50% | 0.5-50% | 0-50% |
| Tc | ≤1% | ≤1% | ≤1% |
| Ti | ≤1% | ≤1% | ≤1% |
| V | ≤1% | ≤1% | ≤1% |
| $Y_2O_3$ | 0-1% | 0-1% | 0-1% |
| $ZrO_2$ | 0.1-3% | 0-3% | 0-3% |
| Ag | 0-5% | 0-5% | 0-5% |
| Al | 0-5% | 0-5% | 0-5% |
| Fe | 0-5% | 0-5% | 0-5% |
| Mg | 0-5% | 0-5% | 0-5% |
| Ni | 0-5% | 0-5% | 0-5% |
| Si | 0-5% | 0-5% | 0-5% |
| CNT | 0-10% | 0-10% | 0-10% |

| Component/Wt. % | Ex. 134 | Ex. 135 | Ex. 136 | Ex. 137 |
|---|---|---|---|---|
| W | 25-88% | 35-87% | 40-86% | 50-85% |
| Cu | 5-68% | 5-57% | 5-51% | 5-40% |
| C | 0.05-0.15% | 0-0.15% | 0-0.15% | 0-0.15% |
| $Cs_2O$ | 0-0.2% | 0-0.2% | 0.04-0.1% | 0-0.2% |
| Hf | 0.8-1.4% | 0-2.5% | 0-2.5% | 0-2.5% |
| $La_2O_3$ | 7-20% | 8-20% | 9-20% | 10-20% |
| Re | 0-40% | 0-40% | 0-40% | 0-40% |
| Ta | 0-50% | 0-50% | 0-50% | 0-50% |
| $Y_2O_3$ | 0-1% | 0-1% | 0.3-0.5% | 0-1% |
| $ZrO_2$ | 0-3% | 0-3% | 0-3% | 0-3% |

| Component/Wt. % | Ex. 138 | Ex. 139 | Ex. 140 |
|---|---|---|---|
| W | 55-88% | 60-87% | 70-86% |
| Cu | 1-34% | 1-28% | 1-17% |
| C | 0-0.15% | 0-0.15% | 0-0.15% |
| $Cs_2O$ | 0-0.2% | 0-0.2% | 0-0.2% |
| Hf | 0-2.5% | 0-2.5% | 0-2.5% |
| $La_2O_3$ | 0-2% | 0-2% | 0-2% |
| Re | 11-40% | 12-40% | 13-40% |
| Ta | 0-50% | 10-50% | 0-50% |

-continued

| | | | |
|---|---|---|---|
| W | 0-50% | 0-50% | 0-50% |
| $Y_2O_3$ | 0-1% | 0-1% | 0-1% |
| $ZrO_2$ | 1.2-1.8% | 0-3% | 0-3% |

| Component/Wt. % | Ex. 141 | Ex. 142 | Ex. 143 |
|---|---|---|---|
| Ti | 55-66% | 65-76% | 70-76% |
| Mo | 20-41% | 20-31% | 20-26% |
| Re | 0-20% | 4-20% | 4-20% |
| Yt | <0.5% | <0.5% | <0.5% |
| Nb | <0.5% | <0.5% | <0.5% |
| Co | <0.5% | <0.5% | <0.5% |
| Cr | <0.5% | <0.5% | <0.5% |
| Zr | <0.5% | <0.5% | <0.5% |
| C | ≤0.15% | ≤0.15% | ≤0.15% |
| O | ≤0.06% | ≤0.06% | ≤0.06% |
| N | ≤20 ppm | ≤20 ppm | ≤20 ppm |

| Component/Wt. % | Ex. 144 | Ex. 145 | Ex. 146 |
|---|---|---|---|
| W | 20-95% | 60-85% | 20-84% |
| Re | 0-47.5% | 15-40% | 5-47.5% |
| Mo | 0-47.5% | <0.5% | 1-47.5% |

| Component/Wt. % | Ex. 147 | Ex. 148 | Ex. 149 |
|---|---|---|---|
| W | 50.1-93% | 65-92% | 70-90% |
| Re | 0-40% | 8-35% | 9-30% |
| Mo | 0-40% | <0.5% | 1-30% |

| Component/Wt. % | Ex. 150 | Ex. 151 | Ex. 152 |
|---|---|---|---|
| W | 20-49% | 20-49% | 20-49% |
| Re | 0-40% | 5-40% | 5-39% |
| Mo | 20-60% | 30-60% | 40-60% |

| Component/Wt. % | Ex. 153 | Ex. 154 | Ex. 155 |
|---|---|---|---|
| W | 20-40% | 20-35% | 20-30% |
| Re | 0-40% | 10-40% | 25-40% |
| Mo | 0-40% | 10-40% | 25-40% |

| Component/Wt. % | Ex. 156 | Ex. 157 | Ex. 158 |
|---|---|---|---|
| W | 20-95% | 60-93% | 20-80% |
| Re | 0-47.5% | 7-40% | 5-47.5% |
| Mo | 0-47.5% | <0.5% | 1-47.5% |
| Cu | <0.5% | <0.5% | <0.5% |
| C | ≤0.15% | ≤0.15% | ≤0.15% |
| Co | ≤0.002% | <0.002% | ≤0.002% |
| $Cs_2O$ | ≤0.2% | ≤0.2% | ≤0.2% |
| Fe | ≤0.02% | ≤0.02% | ≤0.02% |
| H | ≤0.002% | ≤0.002% | <0.002% |
| Hf | <0.5% | <0.5% | <0.5% |
| $La_2O_3$ | <0.5% | <0.5% | <0.5% |
| O | ≤0.06% | ≤0.06% | ≤0.06% |
| Os | <0.5% | <0.5% | <0.5% |
| N | ≤20 ppm | ≤20 ppm | ≤20 ppm |
| Nb | ≤0.01% | ≤0.01% | ≤0.01% |
| Pt | <0.5% | <0.5% | <0.5% |
| S | ≤0.008% | ≤0.008% | ≤0.008% |
| Sn | ≤0.002% | ≤0.002% | ≤0.002% |
| Ta | <0.5% | <0.5% | <0.5% |
| Tc | <0.5% | <0.5% | <0.5% |
| Ti | <0.5% | <0.5% | <0.5% |
| V | <0.5% | <0.5% | <0.5% |
| $Y_2O_3$ | <0.5% | <0.5% | <0.5% |
| Zr | <0.5% | <0.5% | <0.5% |
| $ZrO_2$ | <0.5% | <0.5% | <0.5% |
| Ag | 0-5% | 0-5% | 0-5% |
| Al | 0-5% | 0-5% | 0-5% |
| Fe | 0-5% | 0-5% | 0-5% |
| Mg | 0-5% | 0-5% | 0-5% |
| Ni | 0-5% | 0-5% | 0-5% |
| Si | 0-5% | 0-5% | 0-5% |
| CNT | 0-10% | 0-10% | <0.5% |

-continued

| Component/Wt. % | Ex. 159 | Ex. 160 | Ex. 161 | Ex. 162 |
|---|---|---|---|---|
| Ag | 0-10% | 0-10% | 0-10% | 0-10% |
| Al | 0-10% | 0-10% | 0-10% | 2-10% |
| B | 0-10% | 0-10% | 0-10% | 0-10% |
| Bi | 0-10% | 0-10% | 0-10% | 0-10% |
| Cr | 2-30% | 10-30% | 0-20% | 0-20% |
| Cu | 0-10% | 0-10% | 0-10% | 0-10% |
| Co | 0-10% | 32-70% | 0-10% | 0-10% |
| Fe | 50-80% | 0-20% | 0-10% | 0-10% |
| Hf | 0-10% | 0-10% | 0-10% | 0-10% |
| Ir | 0-10% | 0-10% | 0-10% | 0-10% |
| La | 0-10% | 0-10% | 0-10% | 0-10% |
| Mg | 0-10% | 0-10% | 0-10% | 0-10% |
| Mn | 0-20% | 0-10% | 0-10% | 0-10% |
| Mo | 0-10% | 0-30% | 0-16% | 0-16% |
| Nb | 0-10% | 0-10% | 0-10% | 0-10% |
| Ni | 0.1-30% | 0.1-40% | 0-10% | 0-10% |
| Os | 0-10% | 0-10% | 0-10% | 0-10% |
| Pt | 0-10% | 0-10% | 0-10% | 0-10% |
| Re | 5-40% | 4.8-40% | 4.5-80% | 4.5-80% |
| Rh | 0-10% | 0-10% | 0-10% | 0-10% |
| Se | 0-10% | 0-10% | 0-10% | 0-10% |
| Si | 0-10% | 0-10% | 0-10% | 0-10% |
| Sn | 0-10% | 0-10% | 0-12% | 0-12% |
| Ta | 0-10% | 0-10% | 0-10% | 0-10% |
| Tc | 0-10% | 0-10% | 0-10% | 0-10% |
| Ti | 0-10% | 0-10% | 70-91.5% | 70-91.5% |
| V | 0-10% | 0-10% | 0-10% | 0.01-10% |
| W | 0-10% | 0-20% | 0-10% | 0-10% |
| Y | 0-10% | 0-10% | 0-10% | 0-10% |
| Zr | 0-10% | 0-10% | 0-10% | 0-10% |

| Component/Wt. % | Ex. 163 | Ex. 164 | Ex. 165 | Ex. 166 |
|---|---|---|---|---|
| Ag | 0-10% | 0-10% | 0-10% | 0-10% |
| Al | 0-10% | 0-10% | 0-10% | 0-10% |
| B | 0-10% | 0-10% | 0-10% | 0-10% |
| Bi | 0-10% | 0-10% | 0-10% | 0-10% |
| Cr | 0-10% | 0-20% | 0-20% | 0-10% |
| Cu | 0-10% | 0-10% | 0-50% | 0-10% |
| Co | 0-10% | 0-10% | 0-10% | 0-10% |
| Fe | 0-10% | 0-10% | 0-10% | 0-10% |
| Hf | 0-10% | 0-10% | 0-10% | 0-10% |
| Ir | 0-10% | 0-10% | 0-10% | 0-12% |
| La | 0-10% | 0-10% | 0-10% | 0-10% |
| Mg | 0-10% | 0-10% | 0-10% | 0-10% |
| Mn | 0-10% | 0-10% | 0-10% | 0-10% |
| Mo | 0-55% | 40-93% | 0-50% | 0-20% |
| Nb | 0-10% | 0-10% | 0-10% | 40-85% |
| Ni | 0-45% | 0-10% | 0-10% | 0-10% |
| Os | 0-10% | 0-10% | 0-10% | 0-10% |
| Pt | 0-10% | 0-10% | 0-10% | 0-10% |
| Re | 14-40% | 7-40% | 7-40% | 7-40% |
| Rh | 0-10% | 0-10% | 0-10% | 0-10% |
| Se | 0-10% | 0-10% | 0-10% | 0-10% |
| Si | 0-10% | 0-10% | 0-10% | 0-10% |
| Sn | 0-10% | 0-10% | 0-10% | 0-10% |
| Ta | 35-84% | 0-50% | 0-50% | 0-35% |
| Tc | 0-10% | 0-10% | 0-10% | 0-10% |
| Ti | 0-10% | 0-10% | 0-10% | 0-10% |
| V | 0-10% | 0-10% | 0-10% | 0-10% |
| W | 0.1-25% | 0-50% | 14-10% | 0-15% |
| Y | 0-10% | 0-10% | 0-10% | 0-10% |
| Zr | 0-10% | 0-10% | 0-50% | 0-10% |

| Component/Wt. % | Ex. 167 | Ex. 168 | Ex. 169 | Ex. 170 |
|---|---|---|---|---|
| Ag | 0-10% | 0-10% | 0-5% | 0-5% |
| Al | 0-10% | 0-10% | 0-5% | 5-7% |
| B | 0-10% | 0-10% | 0-5% | 0-5% |
| Bi | 0-10% | 0-10% | 0-5% | 0-5% |
| Cr | 0-10% | 1-95% | 12-28% | 0-5% |
| Cu | 0-10% | 0-10% | 0-5% | 0-5% |
| Co | 0-10% | 0-10% | 36-68% | 0-5% |
| Fe | 0-10% | 0-10% | 0-18% | 0-5% |
| Hf | 0-10% | 0-10% | 0-5% | 0-5% |
| Ir | 0-10% | 0-10% | 0-5% | 0-5% |
| La | 0-10% | 0-10% | 0-5% | 0-5% |

-continued

| | | | | |
|---|---|---|---|---|
| Mg | 0-10% | 0-10% | 0-5% | 0-5% |
| Mn | 0-10% | 0-10% | 0-5% | 0-5% |
| Mo | 0-10% | 0-20% | 0-12% | 0-5% |
| Nb | 0-10% | 0-10% | 0-5% | 0-5% |
| Ni | 30-58% | 0-10% | 9-36% | 0-5% |
| Os | 0-10% | 0-10% | 0-5% | 0-5% |
| Pt | 0-10% | 0-10% | 0-5% | 0-5% |
| Re | 5-40% | 5-40% | 4.8-40% | 4.5-40% |
| Rh | 0-10% | 0-10% | 0-5% | 0-5% |
| Se | 0-10% | 0-10% | 0-5% | 0-5% |
| Si | 0-10% | 0-10% | 0-5% | 0-5% |
| Sn | 0-10% | 0-10% | 0-5% | 0-5% |
| Ta | 0-10% | 0-10% | 0-5% | 0-5% |
| Tc | 0-10% | 0-10% | 0-5% | 0-5% |
| Ti | 30-58% | 0-40% | 0-5% | 70-91.5% |
| V | 0-10% | 0-10% | 0-5% | 3-6% |
| W | 0-10% | 0-10% | 0-16% | 0-5% |
| Y | 0-10% | 0-10% | 0-5% | 0-5% |
| Zr | 0-10% | 0-20% | 0-5% | 0-5% |

| Component/Wt. % | Ex. 171 | Ex. 172 | Ex. 173 | Ex. 174 |
|---|---|---|---|---|
| Ag | 0-8% | 0-8% | 0-8% | 0-8% |
| Al | 0-8% | 0-8% | 0-8% | 2-10% |
| B | 0-8% | 0-8% | 0-8% | 0-8% |
| Bi | 0-8% | 0-8% | 0-8% | 0-8% |
| Cr | 2-30% | 10-30% | 0-20% | 0-20% |
| Cu | 0-8% | 0-8% | 0-8% | 0-8% |
| Co | 0-8% | 32-70% | 0-8% | 0-8% |
| Fe | 50-80% | 0-20% | 0-8% | 0-8% |
| Hf | 0-8% | 0-8% | 0-8% | 0-8% |
| Ir | 0-8% | 0-8% | 0-8% | 0-8% |
| La | 0-8% | 0-8% | 0-8% | 0-8% |
| Mg | 0-8% | 0-8% | 0-8% | 0-8% |
| Mn | 0-20% | 0-8% | 0-8% | 0-8% |
| Mo | 0-8% | 0-30% | 0-16% | 0-16% |
| Nb | 0-8% | 0-8% | 0-8% | 0-8% |
| Ni | 0.1-30% | 0.1-40% | 0-8% | 0-8% |
| Os | 0-8% | 0-8% | 0-8% | 0-8% |
| Pt | 0-8% | 0-8% | 0-8% | 0-8% |
| Re | 5-40% | 4.8-40% | 4.5-80% | 4.5-80% |
| Rh | 0-8% | 0-8% | 0-8% | 0-8% |
| Se | 0-8% | 0-8% | 0-8% | 0-8% |
| Si | 0-8% | 0-8% | 0-8% | 0-8% |
| Sn | 0-8% | 0-8% | 0-12% | 0-12% |
| Ta | 0-8% | 0-8% | 0-8% | 0-8% |
| Tc | 0-8% | 0-8% | 0-8% | 0-8% |
| Ti | 0-8% | 0-8% | 70-91.5% | 70-91.5% |
| V | 0-8% | 0-8% | 0-8% | 0.01-10% |
| W | 0-8% | 0-20% | 0-8% | 0-8% |
| Y | 0-8% | 0-8% | 0-8% | 0-8% |
| Zr | 0-8% | 0-8% | 0-8% | 0-8% |

| Component/Wt. % | Ex. 175 | Ex. 176 | Ex. 177 | Ex. 178 |
|---|---|---|---|---|
| Ag | 0-8% | 0-8% | 0-8% | 0-8% |
| Al | 0-8% | 0-8% | 0-8% | 0-8% |
| B | 0-8% | 0-8% | 0-8% | 0-8% |
| Bi | 0-8% | 0-8% | 0-8% | 0-8% |
| Cr | 0-8% | 0-20% | 0-20% | 0-8% |
| Cu | 0-8% | 0-8% | 0-50% | 0-8% |
| Co | 0-8% | 0-8% | 0-8% | 0-8% |
| Fe | 0-8% | 0-8% | 0-8% | 0-8% |
| Hf | 0-8% | 0-8% | 0-8% | 0-8% |
| Ir | 0-8% | 0-8% | 0-8% | 0-12% |
| La | 0-8% | 0-8% | 0-8% | 0-8% |
| Mg | 0-8% | 0-8% | 0-8% | 0-8% |
| Mn | 0-8% | 0-8% | 0-8% | 0-8% |
| Mo | 0-55% | 40-93% | 0-50% | 0-20% |
| Nb | 0-8% | 0-8% | 0-8% | 40-85% |
| Ni | 0-45% | 0-8% | 0-8% | 0-8% |
| Os | 0-8% | 0-8% | 0-8% | 0-8% |
| Pt | 0-8% | 0-8% | 0-8% | 0-8% |
| Re | 14-40% | 7-40% | 7-40% | 7-40% |
| Rh | 0-8% | 0-8% | 0-8% | 0-8% |
| Se | 0-8% | 0-8% | 0-8% | 0-8% |
| Si | 0-8% | 0-8% | 0-8% | 0-8% |
| Sn | 0-8% | 0-8% | 0-8% | 0-8% |
| Ta | 35-84% | 0-50% | 0-50% | 0-35% |
| Tc | 0-8% | 0-8% | 0-8% | 0-8% |
| Ti | 0-8% | 0-8% | 0-8% | 0-8% |
| V | 0-8% | 0-8% | 0-8% | 0-8% |
| W | 0.1-25% | 0-50% | 14-10% | 0-15% |
| Y | 0-8% | 0-8% | 0-8% | 0-8% |
| Zr | 0-8% | 0-8% | 0-50% | 0-8% |

| Component/Wt. % | Ex. 179 | Ex. 180 | Ex. 181 | Ex. 182 |
|---|---|---|---|---|
| Ag | 0-5% | 0-5% | 0-5% | 0-5% |
| Al | 0-5% | 0-5% | 0-5% | 5-7% |
| B | 0-5% | 0-5% | 0-5% | 0-5% |
| Bi | 0-5% | 0-5% | 0-5% | 0-5% |
| Cr | 0-5% | 1-95% | 12-28% | 0-5% |
| Cu | 0-5% | 0-5% | 0-5% | 0-5% |
| Co | 0-5% | 0-5% | 36-68% | 0-5% |
| Fe | 0-5% | 0-5% | 0-18% | 0-5% |
| H | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 0-5% | 0-20% | 0-12% | 0-5% |
| Nb | 0-5% | 0-5% | 0-5% | 0-5% |
| Ni | 30-58% | 0-5% | 9-36% | 0-5% |
| Os | 0-5% | 0-5% | 0-5% | 0-5% |
| Pt | 0-5% | 0-5% | 0-5% | 0-5% |
| Re | 5-40% | 5-40% | 4.8-40% | 4.5-40% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 0-5% | 0-5% |
| Tc | 0-5% | 0-5% | 0-5% | 0-5% |
| Ti | 30-58% | 0-40% | 0-5% | 70-91.5% |
| V | 0-5% | 0-5% | 0-5% | 3-6% |
| W | 0-5% | 0-5% | 0-16% | 0-5% |
| Y | 0-5% | 0-5% | 0-5% | 0-5% |
| Zr | 0-5% | 0-20% | 0-5% | 0-5% |

In Examples 1-182, it will be appreciated that all of the above ranges include any value between the range and any other range that is between the ranges set forth above. Any of the above values that include the ≤ symbol includes the range from 0 to the stated value and all values and ranges therebetween.

In accordance with another and/or alternative non-limiting aspect of the present disclosure, the weight percent of rhenium plus the weigh percent of the combined weight percentage of bismuth, niobium, tantalum, tungsten, titanium, vanadium, chromium, manganese, yttrium, zirconium, technetium, ruthenium, rhodium, hafnium, osmium, copper, and iridium in the metal alloy can be optionally greater than the weight percent of molybdenum. In one specific non-limiting formulation, the weight percent of rhenium plus the weight percent of the combined weight percentage of bismuth, chromium, iridium, niobium, tantalum, titanium, yttrium, and zirconium in the metal alloy is greater than the weight percent of molybdenum. In another specific non-limiting formulation, the weight percent of rhenium plus the weigh percent of the combined weight percentage of chromium, niobium, tantalum, and zirconium in the metal alloy is greater than the weight percent of molybdenum. In another specific non-limiting formulation, the weight percent of molybdenum in the metal alloy is at least 10 wt. % and less than 50 wt. % (and all values and ranges therebetween). In another specific non-limiting formulation, the weight percent of rhenium in the metal alloy is 41-58.5 wt. % (and all values and ranges therebetween), the weight percent of molybdenum in the metal alloy is at least 15-45 wt. % (and all values and ranges therebetween), and the combined weight percent of bismuth, niobium, tantalum, tungsten, titanium, vanadium, chromium, manganese, yttrium, zirconium, technetium, ruthenium, rhodium, hafnium, osmium, copper, and iridium in the metal alloy is 11-41 wt. % (and all values and ranges therebetween). In another specific non-limiting formulation, the weight percent of rhenium in the metal alloy is 41-58.5 wt. % (and all values and ranges therebetween), the weight percent of molybdenum in the metal alloy is at least 15-45 wt. % (and all values and ranges therebetween), and the combined weight percent of bismuth, chromium, iridium, niobium, tantalum, titanium, yttrium, and zirconium in the metal alloy is 11-41 wt. % (and all values and ranges therebetween). In another specific non-limiting formulation, the weight percent of rhenium in the metal alloy is 41-58.5 wt. % (and all values and ranges therebetween), the weight percent of molybdenum in the metal alloy is at least 15-45 wt. % (and all values and ranges therebetween), and the combined weight percent of chromium, niobium, tantalum, and zirconium in the metal alloy is 11-41 wt. % (and all values and ranges therebetween). In another specific non-limiting embodiment of the invention, the weight percent of rhenium in the metal alloy is greater than the combined weight percent of bismuth, chromium, iridium, niobium, tantalum, titanium, yttrium, and zirconium in the metal alloy. In another specific non-limiting formulation, the weight percent of rhenium in the metal alloy is greater than the combined weight percent of chromium, niobium, tantalum, and zirconium in the metal alloy.

In another and/or alternative non-limiting aspect of the present disclosure, the atomic weight percent of rhenium to the atomic weight percent of the combination of bismuth, niobium, tantalum, tungsten, titanium, vanadium, chromium, manganese, yttrium, zirconium, technetium, ruthenium, rhodium, hafnium, osmium, copper, and iridium can be optionally be 0.7:1 to 1.5:1 (and all values and ranges therebetween), typically 0.8:1 to 1.4:1, more typically 0.8:1 to 1.25:1, and still more typically about 0.9:1 to 1.1:1 (e.g., 1:1). In one specific non-limiting formulation, the atomic weight percent of rhenium to the atomic weight percent of the combination of bismuth, chromium, iridium, niobium, tantalum, titanium, yttrium, and zirconium is 0.7:1 to 5.1:1 (and all values and ranges therebetween), typically 0.8:1 to 1.5:1, more typically 0.8:1 to 1.25:1, and still more typically about 0.9:1 to 1.1:1 (e.g., 1:1). In one specific non-limiting formulation, the atomic weight percent of rhenium to the atomic weight percent of the combination of chromium, niobium, tantalum, and zirconium is 0.7:1 to 5.1:1 (and all values and ranges therebetween), typically 0.8:1 to 1.5:1, more typically 0.8:1 to 1.25:1, and still more typically about 0.9:1 to 1.1:1 (e.g., 1:1).

In another and/or alternative non-limiting aspect of the present disclosure, when the metal alloy includes two of bismuth, niobium, tantalum, tungsten, titanium, vanadium, chromium, manganese, yttrium, zirconium, technetium, ruthenium, rhodium, hafnium, osmium, copper, and iridium, the atomic ratio of the two metals can be optionally be 0.4:1 to 2.5:1 (and all values and ranges therebetween), and typically 0.5:1 to 2:1. In one specific non-limiting formulation, when the metal alloy includes two of bismuth, chromium, iridium, niobium, tantalum, titanium, yttrium, and zirconium, the atomic ratio of the two metals is 0.4:1 to 2.5:1 (and all values and ranges therebetween), and typically 0.5:1 to 2:1. In another specific non-limiting formulation, when the metal alloy includes two of chromium, niobium, tantalum, and zirconium, the atomic ratio of the two metals is 0.4:1 to 2.5:1 (and all values and ranges therebetween), and typically 0.5:1 to 2:1.

In another and/or alternative non-limiting aspect of the present disclosure, the metal alloy optionally includes less than about 5 wt. % (e.g., 0-4.999999 wt. % and all values and ranges therebetween) other metals and/or impurities, typically 0-1 wt. %, more typically 0-0.1 wt. %, even more typically 0-0.01 wt. %, and still even more typically 0-0.001 wt. %. A high purity level of the metal alloy results in the formation of a more homogeneous alloy, which in turn results in a more uniform density throughout the metal alloy, and also results in the desired yield and ultimate tensile strengths of the metal alloy. In one specific non-limiting formulation, the metal alloy is formed of rhenium plus at least two metals selected from the group of molybdenum, bismuth, niobium, tantalum, tungsten, titanium, vanadium, chromium, manganese, yttrium, zirconium, technetium, ruthenium, rhodium, hafnium, osmium, copper, and iridium, and the content of metal alloy that includes other elements and compounds is 0-0.1 wt. %, typically 0-0.01 wt. %, and more typically 0-0.001 wt. %. In another specific non-limiting formulation, the metal alloy is formed of rhenium plus at least two metals selected from the group of molybdenum, bismuth, chromium, iridium, niobium, tantalum, titanium, yttrium, and zirconium, and the content of metal alloy that includes other elements and compounds is 0-0.1 wt. %, typically 0-0.01 wt. %, and more typically 0-0.001 wt. %. In another specific non-limiting formulation, the metal alloy is formed of rhenium plus at least three metals selected from the group of rhenium, molybdenum, chromium, niobium, tantalum, and zirconium, and the content of metal alloy that includes other elements and compounds is 0-0.1 wt. %, typically 0-0.01 wt. %, and more typically 0-0.001 wt. %.

In another and/or alternative non-limiting aspect of the present disclosure, the bone plate and/or fastener system is made from a refractory metal alloy that allows the thickness of the bone plate and/or fastener system to be thinner than standard stainless steel, standard cobalt-chromium alloys, and standard titanium alloys. When the bone plate and/or fastener system is partially or fully formed of a refractory metal alloy, the mechanical characteristics of the bone plate and/or fastener system are superior to competitive products made of standard stainless steel, standard cobalt-chromium alloys, and standard titanium alloys. The superior mechanical characteristics of the bone plate and/or fastener system that includes refractory metal alloy can be used to form a bone plate and/or fastener system that is much narrower and/or thinner than bone plate and/or fastener systems formed of standard stainless steel, standard cobalt-chromium alloys, and standard titanium alloys.

In another and/or alternative non-limiting aspect of the present disclosure, the use of refractory metal alloy or a metal alloy that includes at least 15 awt. % rhenium to at least partially form the bone plate and/or fastener system can thus 1) increase the radiopacity of the bone plate and/or fastener system, 2) increase the radial strength of the bone plate and/or fastener system, 3) increase the yield strength and/or ultimate tensile strength of the bone plate and/or fastener system, 4) improve the stress-strain properties of the bone plate and/or fastener system, 5) improve the strength and/or durability of the bone plate and/or fastener system, 6) increase the hardness of the bone plate and/or fastener system, 7) improve the biostability and/or biocompatibility properties of the bone plate and/or fastener system, 8) resist cracking in the bone plate and/or fastener system and resist propagation of cracks, 9) increase yield strength of the bone plate and/or fastener system, 10) improve durability of the bone plate and/or fastener system, 11) reduce adverse tissue reactions after implant of the bone plate and/or fastener system, 12) reduce metal ion release after implant of the bone plate and/or fastener system, 13) reduce corrosion of the bone plate and/or fastener system, 14) reduce allergic reaction after implant of the bone plate and/or fastener system, 15) improve hydrophilicity of the bone plate and/or fastener system, 16) improve ductility of the bone plate and/or fastener system, and/or 17) reduce toxicity of the bone plate and/or fastener system after implant of the bone plate and/or fastener system. The bone plate and/or fastener system generally includes one or more materials that impart the desired properties to the bone plate and/or fastener system to function properly and effectively and to withstand the manufacturing processes needed to produce the bone plate and/or fastener system. These manufacturing processes can include, but are not limited to, laser cutting, etching, annealing, drawing, pilgering, electroplating, electro-polishing, machining, plasma coating, 3D printed coatings, 3D printing, chemical vapor deposition, chemical polishing, cleaning, pickling, ion beam deposition or implantation, sputter coating, vacuum deposition, etc. In one non-limiting embodiment, at least a portion or all of the bone plate and/or fastener system is formed by a 3D printing process.

In another and/or alternative non-limiting aspect of the present disclosure, the metal alloy used to partially or fully form the bone plate and/or fastener system can be nitrided; however, this is not required. After the metal alloy is nitrided, the refractory metal alloy is typically cleaned; however, this is not required. During the nitriding process, the surface of the metal alloy is modified by the presence of nitrogen. The nitriding process can be by gas nitriding, salt bath nitriding, or plasma nitriding. In gas nitriding, the nitrogen diffuses onto the surface of the metal alloy, thereby creating a nitrided layer.

In yet another and/or alternative non-limiting aspect of the present disclosure, the bone plate and/or fastener system can include, contain, and/or be coated with one or more agents that facilitate in the success of the bone plate and/or fastener system and/or treated area. The term "agent" includes, but is not limited to a substance, pharmaceutical, biologic, veterinary product, drug, and analogs or derivatives otherwise formulated and/or designed to prevent, inhibit and/or treat one or more clinical and/or biological events, and/or to promote healing. Non-limiting examples of clinical events that can be addressed by one or more agents include, but are not limited to, viral, fungal, and/or bacterial infection; vascular diseases and/or disorders; digestive diseases and/or disorders; reproductive diseases and/or disorders; lymphatic diseases and/or disorders; cancer; implant rejection; pain; nausea; swelling; arthritis; bone diseases and/or disorders; organ failure; immunity diseases and/or disorders; cholesterol problems; blood diseases and/or disorders; lung diseases and/or disorders; heart diseases and/or disorders; brain diseases and/or disorders; neuralgia diseases and/or disorders; kidney diseases and/or disorders; ulcers; liver diseases and/or disorders; intestinal diseases and/or disorders; gallbladder diseases and/or disorders; pancreatic diseases and/or disorders; psychological disorders; respiratory diseases and/or disorders; gland diseases and/or disorders; skin diseases and/or disorders; hearing diseases and/or disorders; oral diseases and/or disorders; nasal diseases and/or disorders; eye diseases and/or disorders; fatigue; genetic diseases and/or disorders; burns; scarring and/or scars; trauma; weight diseases and/or disorders; addiction diseases and/or disorders; hair loss; cramps; muscle spasms; tissue repair; nerve repair; neural regeneration and/or the like. The type and/or amount of agent included in and/or coated on the bone plate and/or fastener system can vary. When two or more agents are included in and/or coated on the bone plate and/or fastener system, the amount of two or more agents can be the same or different. The type and/or amount of agent included on, in, and/or in conjunction with bone plate and/or fastener system are generally selected to address one or more clinical events. Typically, the amount of agent included on, in, and/or used in conjunction with the bone plate and/or fastener system is about 0.01-100 ug per $mm^2$ and/or at least about 0.00001 wt. % of device; however, other amounts can be used. In one non-limiting embodiment of the disclosure, the bone plate and/or fastener system can be partially or fully coated and/or impregnated with one or more agents to facilitate in the success of a particular medical procedure. The amount of the two of more agents on, in, and/or used in conjunction with the bone plate and/or fastener system can be the same or different. The one or more agents can be coated on and/or impregnated in the bone plate and/or fastener system by a variety of mechanisms such as, but not limited to, spraying (e.g., atomizing spray techniques, etc.), flame spray coating, powder deposition, dip coating, flow coating, dip-spin coating, roll coating (direct and reverse), sonication, brushing, plasma deposition, depositing by vapor deposition, MEMS technology, and rotating mold deposition.

In a further and/or alternative non-limiting aspect of the present disclosure, the one or more agents on and/or in the bone plate and/or fastener system (when used) can be released in a controlled manner so the area to be treated is provided with the desired dosage of agent over a sustained period of time. As can be appreciated, controlled release of one or more agents on the bone plate and/or fastener system is not always required and/or desirable. As such, one or more of the agents on and/or in the bone plate and/or fastener system can be uncontrollably released from the bone plate and/or fastener system during and/or after insertion of the bone plate and/or fastener system in the treatment area. It can also be appreciated that one or more agents on and/or in the bone plate and/or fastener system can be controllably released from the bone plate and/or fastener system and one or more agents on and/or in the bone plate and/or fastener system can be uncontrollably released from the bone plate and/or fastener system. It can also be appreciated that one or more agents on and/or in one region of the bone plate and/or fastener system can be controllably released from the bone plate and/or fastener system and one or more agents on and/or in the bone plate and/or fastener system can be uncontrollably released from another region on the bone plate and/or fastener system. As such, the bone plate and/or fastener system can be designed such that 1) all the agent on and/or in the bone plate and/or fastener system is controllably released, 2) some of the agent on and/or in the bone plate and/or fastener system is controllably released and some of the agent on the bone plate and/or fastener system is non-controllably released, or 3) none of the agent on and/or in the bone plate and/or fastener system is controllably released. The bone plate and/or fastener system can also be designed such that the rate of release of the one or more agents from the bone plate and/or fastener system is the same or different. The bone plate and/or fastener system can also be designed such that the rate of release of the one or more agents from one or more regions on the bone plate and/or fastener system is the same or different. Non-limiting arrangements that can be used to control the release of one or more agents from the bone plate and/or fastener system include 1) at least partially coating one or more agents with one or more polymers, 2) at least partially incorporating and/or at least partially encapsulating one or more agents into and/or with one or more polymers, and/or 3) inserting one or more agents in pores, passageway, cavities, etc., in the bone plate and/or fastener system and at least partially coating or covering such pores, passageway, cavities, etc., with one or more polymers. As can be appreciated, other or additional arrangements can be used to control the release of one or more agents from the bone plate and/or fastener system.

In another and/or alternative non-limiting aspect of the present disclosure, the bone plate and/or fastener system, when including and/or coated with one or more agents, can include and/or be coated with one or more agents that are the same or different in different regions of the bone plate and/or fastener system and/or have differing amounts and/or concentrations in differing regions of the bone plate and/or fastener system. For instance, the bone plate and/or fastener system can be 1) coated with and/or include one or more biologicals on at least one portion of the bone plate and/or fastener system and at least another portion of the bone plate and/or fastener system is not coated with and/or includes agent; 2) coated with and/or include one or more biologicals on at least one portion of the bone plate and/or fastener system that is different from one or more biologicals on at least another portion of the bone plate and/or fastener system; and/or 3) coated with and/or include one or more biologicals at a concentration on at least one portion of the bone plate and/or fastener system that is different from the concentration of one or more biologicals on at least another portion of the bone plate and/or fastener system; etc.

In still yet another and/or alternative non-limiting aspect of the present disclosure, one or more portions of the bone plate and/or fastener system can 1) include the same or different agents, 2) include the same or different amount of one or more agents, 3) include the same or different polymer coatings, 4) include the same or different coating thicknesses of one or more polymer coatings, 5) have one or more portions of the bone plate and/or fastener system controllably release and/or uncontrollably release one or more agents, and/or 6) have one or more portions of the bone plate and/or fastener system controllably release one or more agents and one or more portions of the bone plate and/or fastener system uncontrollably release one or more agents.

In yet another and/or alternative non-limiting aspect of the disclosure, the bone plate and/or fastener system can include a marker material that facilitates enabling the bone plate and/or fastener system to be properly positioned in a body passageway. The marker material is typically designed to be visible to electromagnetic waves (e.g., x-rays, microwaves, visible light, infrared waves, ultraviolet waves, etc.); sound waves (e.g., ultrasound waves, etc.); and/or magnetic waves (e.g., MRI, etc. In one non-limiting embodiment, the marker material is visible to x-rays (i.e., radiopaque). The marker material can form all or a portion of the bone plate and/or fastener system and/or be coated on one or more portions (flaring portion and/or body portion, at ends of bone plate and/or fastener system, at or near transition of body portion and flaring section, etc.) of the bone plate and/or fastener system. The location of the marker material can be on one or multiple locations on the bone plate and/or fastener system. The size of the one or more regions that include the marker material can be the same or different. The marker material can be spaced at defined distances from one another to form ruler-like markings on the bone plate and/or fastener system to facilitate in the positioning of the bone plate and/or fastener system in a body passageway.

The bone plate and/or fastener system can include one or more surface structures (e.g., pore, channel, pit, rib, slot, notch, bump, teeth, needle, well, hole, groove, etc.). These structures can be at least partially formed by MEMS (e.g., micro-machining, etc.) technology and/or other types of technology.

The bone plate and/or fastener system can include one or more micro-structures (e.g., micro-needle, micro-pore, micro-cylinder, micro-cone, micro-pyramid, micro-tube, micro-parallelepiped, micro-prism, micro-hemisphere, teeth, rib, ridge, ratchet, hinge, zipper, zip-tie like structure, etc.) on the surface of the bone plate and/or fastener system. As defined herein, a "micro-structure" is a structure that has at least one dimension (e.g., average width, average diameter, average height, average length, average depth, etc.) that is no more than about 2 mm, and typically no more than about 1 mm. As can be appreciated, when the bone plate and/or fastener system includes one or more surface structures, 1) all the surface structures can be micro-structures, 2) all the surface structures can be non-micro-structures, or 3) a portion of the surface structures can be micro-structures and a portion can be non-micro-structures. Non-limiting examples of structures that can be formed on the bone plate and/or fastener systems are illustrated in United States Patent Publication Nos. 2004/0093076 and 2004/0093077, which are incorporated herein by reference.

In still yet another and/or alternative non-limiting aspect of the present disclosure, there is provided a near net process for a body or other metal component of the bone plate and/or fastener system. In one non-limiting embodiment of the disclosure, there is provided a method of powder pressing materials and increasing the strength post sintering by imparting additional cold work. In one non-limiting embodiment, the green part is pressed and then sintered. Thereafter, the sintered part is again pressed to increase its mechanical strength by imparting cold work into the pressed and sintered part. Generally, the temperature during the pressing process after the sintering process is 20-100° C. (and all values and ranges therebetween), typically 20-80° C., and more typically 20-40° C. As defined herein, cold working occurs at a temperature of no more than 150° C. (e.g., 10-150° C. and all values and ranges therebetween). The change in the shape of the repressed post-sintered part needs to be determined so the final part (pressed, sintered and re-pressed) meets the dimensional requirements of the final formed part. For a Mo47.5Re alloy, MoRe alloy, ReW alloy, molybdenum alloy, tungsten alloy, rhenium alloy, other type of refractory metal alloy, or TWIP alloy formed of a high titanium content, a prepress pressure of 1-300 tsi (1 ton per square inch) (and all values and ranges therebetween) can be used followed by a sintering process of at least 1600° C. (e.g., 1600-2600° C. and all values and ranges therebetween) and a post sintering press at a pressure of 1-300 tsi (and all values and ranges therebetween) at a temperature of at least 20° C. (e.g., 20-100° C. and all values and ranges therebetween; 20-40° C., etc.). There is also provided a process of increasing the mechanical strength of a pressed metal part by repressing the post-sintered part to add additional cold work into the material, thereby increasing its mechanical strength. There is also provided a process of powder pressing to a near net or final part using metal powder. In one non-limiting embodiment, the metal powder used to form the near net or final part includes a minimum of 40% rhenium by weight and at least 30% molybdenum, and the remainder can optionally include one or more elements of tungsten, tantalum, zirconium, iridium, titanium, bismuth, and yttrium. In another non-limiting embodiment, the metal powder used to form the near net or final part includes 20-80 wt. % rhenium (and all values and ranges therebetween), 20-80 wt. % molybdenum (and all values and ranges therebetween), and optionally one or more elements of tungsten, tantalum, zirconium, iridium, titanium, bismuth, and yttrium. In another non-limiting embodiment, the metal powder used to form the near net or final part includes tungsten (20-60 wt. % and all values and ranges therebetween), rhenium (20-80 wt. % and all values and ranges therebetween) and one or more other elements 0-5 wt. % (and all values and ranges therebetween). In another non-limiting embodiment, the metal powder used to form the near net or final part includes tungsten (20-80 wt. % and all values and ranges therebetween), rhenium (20-80 wt. % and all values and ranges therebetween), molybdenum (0-15 wt. % and all values and ranges therebetween), and one or more other elements 0-5 wt. % (and all values and ranges therebetween). In another non-limiting embodiment, the metal powder used to form the near net or final part includes tungsten (20-80 wt. % and all values and ranges therebetween), copper (1-30 wt. % and all values and ranges therebetween), and one or more other elements 0-5 wt. % (and all values and ranges therebetween). In another non-limiting embodiment, the metal powder used to form the near net or final part includes a titanium alloy or a cobalt alloy. The ductility of the refractory metal alloy measured as % reduction in area can increase and yield and ultimate tensile strength can increase.

In one non-limiting object of the present disclosure, there is the provision of an orthopedic fixation device for fracture fixation comprising a bone plate body having a plurality of screw openings therethrough; at least one of the screw openings as viewed along a central longitudinal axis of said screw opening having a plurality of plastically deformable protruding surfaces and a plurality of arcuate recessed regions; each arcuate recess region located between two protruding surfaces; an interior of the screw openings absent threads.

In another and/or alternative non-limiting object of the present disclosure, there is the provision of an orthopedic fixation device wherein each of the protruding surfaces extends no more than 10% about a perimeter of the screw opening; and/or each of the arcuate recessed regions extends no more than 10% about the perimeter of the screw opening.

In another and/or alternative non-limiting object of the present disclosure, there is the provision of an orthopedic fixation device wherein one or more of the protruding surfaces is formed of top and bottom sloped surfaces; each of the top sloped surfaces slopes downwardly from a top edge or a top region of the screw opening and terminates at a location that is ±0-20% a mid-depth of the screw opening; each of the bottom sloped surfaces slopes upwardly from a bottom edge or a bottom region of the screw opening and terminates at a location that is 0-20% said mid-depth of the screw opening.

In another and/or alternative non-limiting object of the present disclosure, there is the provision of an orthopedic fixation device wherein at least one of the top sloped surfaces is positioned above at least one of the top sloped surfaces.

In another and/or alternative non-limiting object of the present disclosure, there is the provision of an orthopedic fixation device wherein at least one of the top and bottom sloped surfaces have a same shape and size.

In another and/or alternative non-limiting object of the present disclosure, there is the provision of an orthopedic fixation device wherein at least one of the top and bottom sloped surfaces has three sides.

In another and/or alternative non-limiting object of the present disclosure, there is the provision of an orthopedic fixation device wherein at least one of the intermediate sloped surfaces has four sides.

In another and/or alternative non-limiting object of the present disclosure, there is the provision of an orthopedic fixation device wherein a thickness of an end of at least one of the protruding surfaces is thinner than at other regions of the protruding surface.

In another and/or alternative non-limiting object of the present disclosure, there is the provision of an orthopedic fixation device wherein a thickest region of at least one of the protruding surfaces is located adjacent an inner wall of the screw opening.

In another and/or alternative non-limiting object of the present disclosure, there is the provision of an orthopedic fixation device wherein a thickness of at least one of the protruding surfaces progressively decreases from a location adjacent the inner wall of the screw opening to the end of said protruding surface that is located closest to a central axis of the screw opening.

In another and/or alternative non-limiting object of the present disclosure, there is the provision of an orthopedic fixation device wherein the deformable protruding surfaces are symmetrically oriented about an outer perimeter of the screw opening, and the arcuate recessed regions are symmetrically oriented about an outer perimeter of the screw opening.

In another and/or alternative non-limiting object of the present disclosure, there is the provision of an orthopedic fixation device wherein the bone plate body includes multiple arcuate regions on each side of the bone plate body such that a width of the bone plate body varies along a longitudinal length of the bone plate body; a location of the screw openings on the bone plate body represents a larger width of the bone plate body than regions of the bone plate body that are absent the screw openings.

In another and/or alternative non-limiting object of the present disclosure, there is the provision of an orthopedic fixation device wherein the bone plate body is at least partially formed of a refractory alloy or a metal alloy that includes at least 15 awt. % rhenium.

In another and/or alternative non-limiting object of the present disclosure, there is the provision of an orthopedic fixation device for fracture fixation comprising a bone plate body having a plurality of screw openings therethrough; at least one of the screw openings includes a lead thread plate and at least one bottom thread located below the lead thread plate; the lead thread plate includes a plurality of lead recesses; each of the lead recesses is spaced from one another by a wide portion, a top surface of the lead thread plate is positioned parallel to a top surface of the bone plate body.

In another and/or alternative non-limiting object of the present disclosure, there is the provision of an orthopedic fixation device wherein the bone plate body is planar along the longitudinal axis of the bone plate body.

In another and/or alternative non-limiting object of the present disclosure, there is the provision of an orthopedic fixation device wherein the bone plate body has a curved profile along a lateral axis of the bone plate body and about a central longitudinal axis of the bone plate body.

In another and/or alternative non-limiting object of the present disclosure, there is the provision of an orthopedic fixation device wherein a minimum width of one or more of the lead recesses is less than a maximum width of the bottom threads located below the lead thread plate.

In another and/or alternative non-limiting object of the present disclosure, there is the provision of an orthopedic fixation device wherein a maximum width of one or more of the wide portions of the lead thread plate is greater than a maximum width of the bottom threads located below the lead thread plate.

In another and/or alternative non-limiting object of the present disclosure, there is the provision of an orthopedic fixation device wherein the lead recesses are spaced symmetrically about the screw opening from one another.

In another and/or alternative non-limiting object of the present disclosure, there is the provision of an orthopedic fixation device wherein the wide portions are spaced symmetrically about the screw opening from one another.

In another and/or alternative non-limiting object of the present disclosure, there is the provision of an orthopedic fixation device wherein the top surface of the lead thread plate is recessed from the top surface of the bone plate body, a recess wall extends upwardly from the top surface of the lead thread plate to the top surface of the bone plate body.

In another and/or alternative non-limiting object of the present disclosure, there is the provision of an orthopedic fixation device wherein a maximum cross-sectional area of the top surface of the lead thread plate is greater than a maximum cross-sectional area of a region under the lead thread plate.

In another and/or alternative non-limiting object of the present disclosure, there is the provision of an orthopedic fixation device wherein the bone plate body includes a non-threaded screw opening; the non-threaded screw opening is absent a lead thread plate and threading; the non-threaded screw opening is positioned between two screw openings; the non-threaded screw opening includes a slope surface that slopes downwardly from the top surface of the bone plate body; the slope surface does not fully encircle the non-threaded screw opening.

In another and/or alternative non-limiting object of the present disclosure, there is the provision of an orthopedic fixation device further including a fastener arrangement that is configured to be secured to one of the screw openings; the fastener arrangement includes a head portion and a body portion connected to the bottom of the head portion and extends downwardly from the head portion; the head portion includes head threading on an outer surface of the head portion; the body portion includes body threading on an outer surface of the body portion, one or more of a) a pitch of the body threading is different from a pitch of the head threading, b) a thread length of the body threading is different from a thread length of the head threading, c) a thread angle of the body threading is different from a thread angle of the head threading, d) a root depth of the body threading is different from a root depth of the head threading, and/or e) a lead of the body threading is different from a lead of the head threading.

In another and/or alternative non-limiting object of the present disclosure, there is the provision of an orthopedic fixation device wherein the head portion of the fastener arrangement includes a tapered portion that forms a tapered profile of the head portion along a central axis of said the portion; the head threading is at least partially located on the tapered portion; the tapered portion constitutes 20-100% of a longitudinal length of the head portion.

In another and/or alternative non-limiting object of the present disclosure, there is the provision of an orthopedic fixation device wherein an angle of taper of the tapered portion is constant along 60-100% of the tapered portion.

In another and/or alternative non-limiting object of the present disclosure, there is the provision of an orthopedic fixation device wherein the head threading on the tapered portion has a tapered profile.

These and other objects and advantages will become apparent from the discussion of the distinction between the disclosure and the prior art and when considering the non-limiting embodiment illustrated in the accompanying drawings.

BRIEF DESCRIPTION OF THE DRAWINGS

The above and other features and advantages of the disclosure will become apparent from a consideration of the subsequent detailed description presented in connection with the accompanying drawings in which.

DESCRIPTION OF NON-LIMITING EMBODIMENTS

Figure 1:
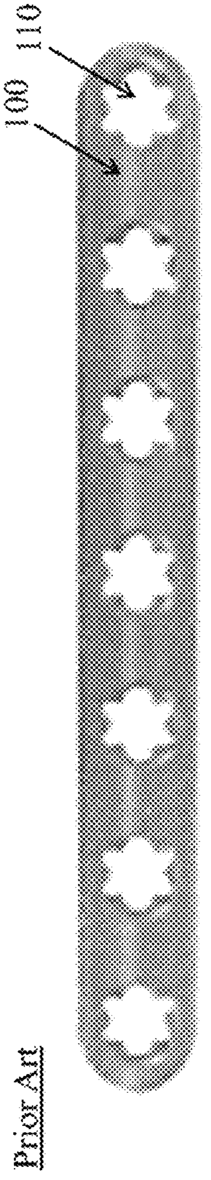
FIG. 1 is an illustration of a prior art bone plate.

A more complete understanding of the articles/devices, processes and components disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any unavoidable impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The terms "about" and "approximately" can be used to include any numerical value that can vary without changing the basic function of that value. When used with a range, "about" and "approximately" also disclose the range defined by the absolute values of the two endpoints, e.g. "about 2 to about 4" also discloses the range "from 2 to 4." Generally, the terms "about" and "approximately" may refer to plus or minus 10% of the indicated number.

Percentages of elements should be assumed to be percent by weight of the stated element, unless expressly stated otherwise.

Referring now to FIG. 1, there is illustrated a prior art bone plate 100 that has seven star-shaped screw openings 110 that are cut uniformly through the fully thickness of the bone plate 100.

Referring new to FIGS. 2-23, there is illustrated a novel bone plate and fastener arrangement that can be used on various bones such as, but not limited to, a radius, an ulna, spinal bones, maxillofacial bones, a fibula, metatarsal bones, calcaneus bones, ankle bones, femur, distal tibia, proximal tibia, proximal humerus, distal humerus, a clavicle, bones of the foot, bones of the hand, etc. The bone plate can be shaped to match a particular bone surface (e.g., I-shaped, L-shape, T-shape, Y-shape, S-shape, C-shaped, E-shaped, F-shaped, J-shaped, U-shaped, etc.) and any other appropriate shape to fit the bone to be treated. In one non-limiting embodiment the bone plate can have a planar or non-planar profile along the longitudinal length of the bone plate. In another non-limiting embodiment, the bone plate can have a planar or non-planar profile along lateral axis of the bone plate along one or more locations or along the complete longitudinal length of the bone plate. The thickness of the bone plate can be constant or vary along the longitudinal length of the bone plate. In one non-limiting embodiment, the thickness of the bone plate is generally constant along 80-100% (and all values and ranges therebetween) of the longitudinal length of the bone plate. One or more surface of the bone plate can optionally be formed by a cutting process, stamping process, 3D printer, molding process, etc.

The novel bone plate and/or novel fastener arrangement can be made of a metal alloy (e.g., refractory metal alloy, metal alloy that includes at least 15 awt. % rhenium, etc.). The novel bone plate and/or novel fastener arrangement can be configured to penetrate and affix the bone plate to a bone while enabling multiple directions of the fastener arrangement axis relative to the normal vector of the bone plate, which facilitates fusion by stabilizing sections of bone together. The novel bone plate allows for a wide range of fastener arrangement locking angulation, thus providing greater surgical options during bone repairing procedures.

Figure 2:
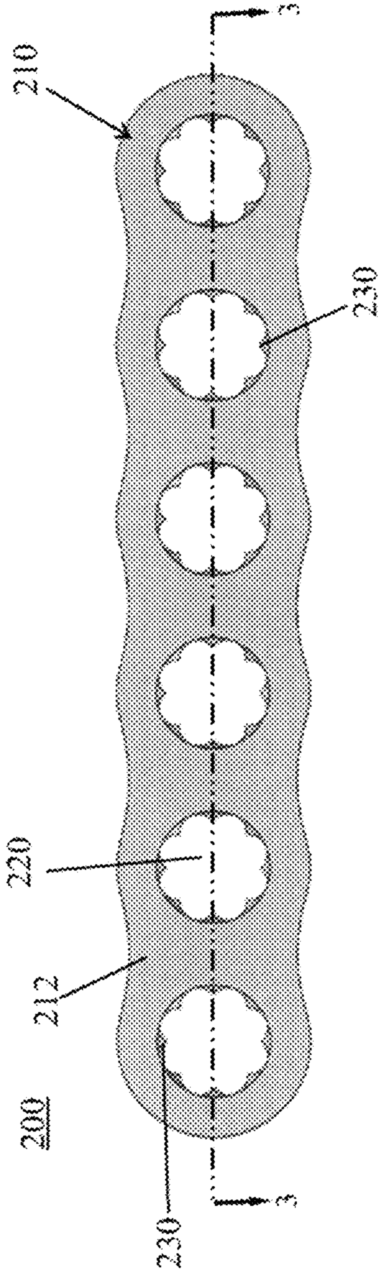
FIG. 2 is a top plan view of a one non-limiting embodiment of the bone plate in accordance with the present disclosure.

Referring now to FIGS. 2-8, there is illustrated bone plate 200 in accordance with the present disclosure. The bone plate 200 is configured to provide a bone fixation assembly that can accept a fastener arrangement 290 (e.g., screws, etc.). Bone plate 200 has a body 210 that has a lower surface 214 and an upper surface 212, a central longitudinal axis, a lateral axis that is traverse to the central longitudinal axis, and one or more screw openings 220 that extend from lower surface 214 to upper surface 212. The shape and/or size of the screw openings 220 can be the same or different. As illustrated in FIG. 2, the shape and size of all of the screw openings 220 are the same. The spacing of adjacently positioned screw openings 220 can be the same or different. As illustrated in FIG. 2, the spacing of adjacently positioned screw openings 220 are the same. The screw openings 220 are spaced from the peripheral edge of the bone plate 200.

The one or more screw openings 210 in body 210 of bone plate 200 are shown as having a central axis, and the screw openings 220 are adapted to receive the fastener arrangement 290.

The geometry of the screw openings 220 in the body 210 of bone plate 200 optionally allows for plastic deformation of the screw opening geometry to lock a portion of the head portion of the fastener arrangement 290 in the screw opening 220. This locked construct of the head portion of the fastener arrangement 290 and screw opening 220 in bone plate 200 can be used to stabilize the bones relative to bone plate 200 and facilitate fusion.

Figure 3:
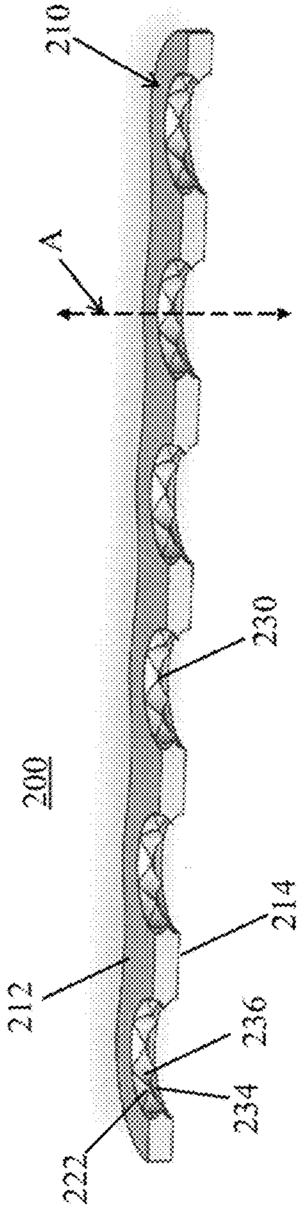
FIG. 3 is a cross-sectional view of the bone plate along line 3-3 of FIG. 2.
Figure 4:
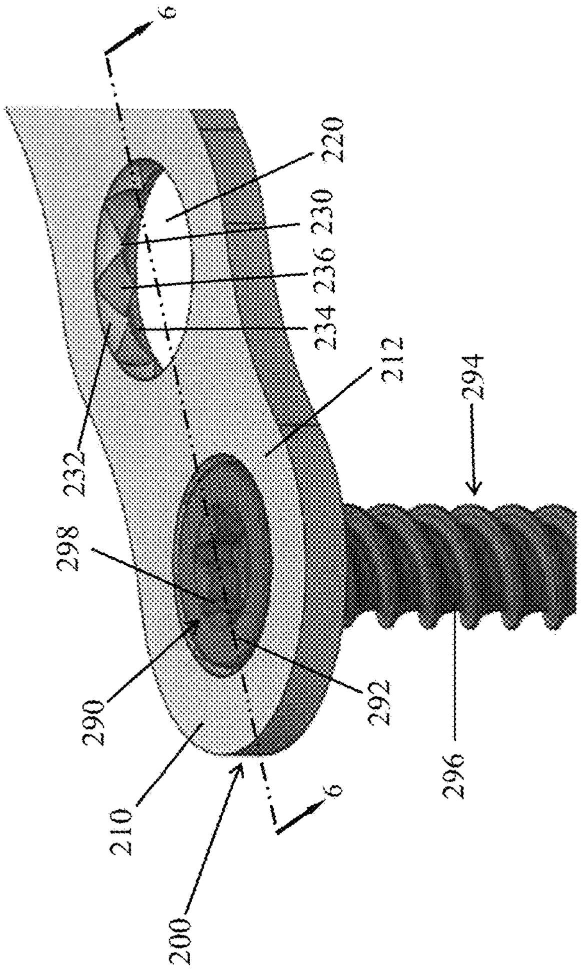
FIG. 4 is an enlarged end portion of the bone plate of FIG. 1 and includes an upper portion of a screw positioned in the screw opening of the bone plate.
Figure 6:
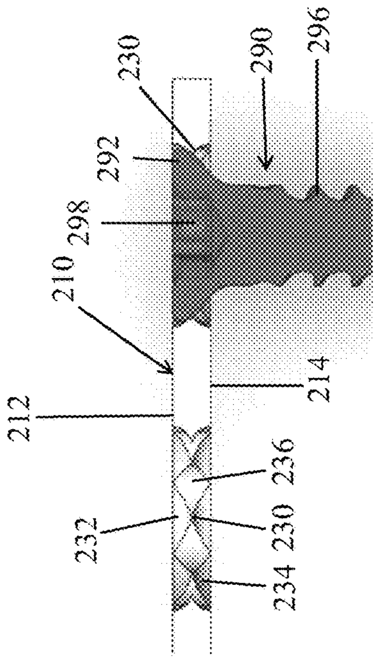
FIG. 6 is a cross-sectional view of the bone plate along line 6-6 of FIG. 4.

The screw openings 220 generally have a circular cross-sectional shape and the inner surface of screw openings 220 include a series of inwardly-protruding surfaces 230. The plurality of protruding surfaces 230 extend into screw opening 220 toward the central axis A of screw opening 220 and are spaced from central axis A of screw opening 220. The plurality of protruding surfaces 230 are illustrated as forming smooth and non-threaded surfaces One non-limiting purpose of plurality of protruding surfaces 230 is to engage one or more portions of the head of a fastener arrangement (e.g., screw, etc.) to facilitate in securing head portion 292 of fastener arrangement 290 to bone plate 200. The protruding surfaces 230 are configured to be plastically deformed when head portion 292 of fastener arrangement 290 is partially or fully inserted into screw opening 220. The plastic deformation and frictional engagement between head portion 292 of fastener arrangement 290 and protruding surfaces 230 results in head portion 292 of fastener arrangement 290 to be secured to bone plate 200 when fastener arrangement 290 is partially or fully inserted into screw openings 220. As illustrated in FIGS. 3, 4 and 6, screw opening 220 is absent threads and only the plastic deformation and frictional engagement between head portion 292 of fastener arrangement 290 and protruding surfaces 230 in screw opening 220 are used to secure head portion 292 of fastener arrangement 290 to bone plate 200. In such an arrangement, head portion 292 of fastener arrangement 290 may or may not include threading since any threading on head portion 292 of fastener arrangement 290 will not be engaging any thread in screw opening 220.

Figure 5:
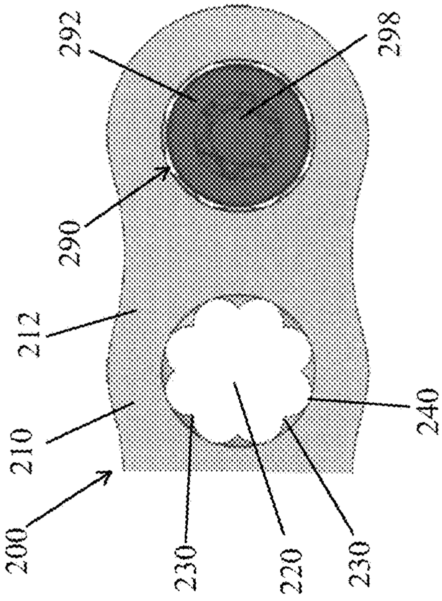
FIG. 5 is a top plan view of FIG. 4.

As illustrated in FIG. 2, each of the screw openings 220 includes eight (8) protruding surfaces 230 when screw opening 220 is viewed along its central axis. When screw opening 220 is along the central axis A, an arcuate recessed region 240 is located on both sides of protruding surface 230 as illustrated in FIG. 5.

Each protruding surfaces 230 is formed by a top sloped surface 232 and a bottom sloped surface 234. Positioned between each set of top and bottom sloped surfaces 232, 234 is an intermediate sloped surface 236 that partially or fully forms the arcuate recessed region 240. Each of sloped surfaces 232, 234, 236 extend no more than 20% (e.g., 2-20% and all values and ranges therebetween) about a perimeter of screw opening 220.

As illustrated in FIGS. 3, 4 and 6, top sloped surfaces 232 slope downwardly from a top edge or a top region of screw opening 220 and terminate at a location that is ±0-20% (and all values and ranges therebetween) of the mid-depth of screw opening 220. As also illustrated in FIGS. 3, 4 and 6, bottom sloped surfaces 234 slope upwardly from a bottom edge or a bottom region of screw opening 220 and terminate at a location that is ±0-20% (and all values and ranges therebetween) the mid-depth of screw opening 220.

As illustrated in FIGS. 3, 4 and 6, top sloped surfaces 232 and bottom sloped surfaces 234 have a similar shape and a similar size. Each of top sloped surfaces 232 is positioned above a bottom sloped surface 234 and each set of top and bottom slope surfaces 232, 234 form first protruding surface 230. An intermediate sloped surface 236 is positioned between each pair of top and bottom slope surfaces 232, 234. Each of the top and bottom sloped surfaces 232, 234 have three sides, and each of intermediate sloped surfaces 236 have four sides. As illustrated FIGS. 3, 4 and 6, each of intermediate sloped surfaces 236 extends from the top edge or the top region of screw opening 220 to the bottom edge or the bottom region of screw opening 220.

Protruding surfaces 230 can be formed by a cutting process, stamping process, 3D printer, molding process, etc. The radius of curvature of a top sloped surface 232, a bottom slope surface 234, and an intermediate sloped surfaces 236 is non-limiting.

The thickness of the end of protruding surface 230 is thinner than the other portions of protruding surface 230 to enable the end region of the protruding surface 230 to at least partially plastically deform when a head portion 292 of a fastener arrangement 290 is secured to bone plate 200.

As illustrated in FIGS. 2 and 5, protruding surfaces 230 are symmetrically oriented about the inner surface of screw opening 220.

Figure 8:
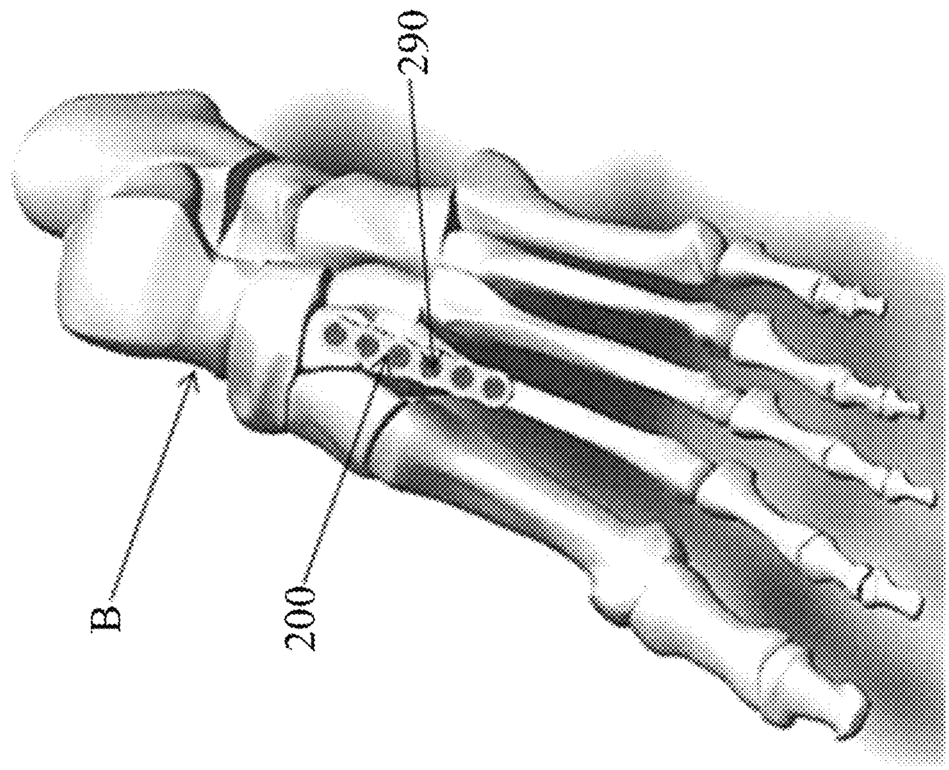
FIG. 8 illustrates the bone plate of FIG. 2 positioned and screwed by screws on a bone structure.
Figure 7:
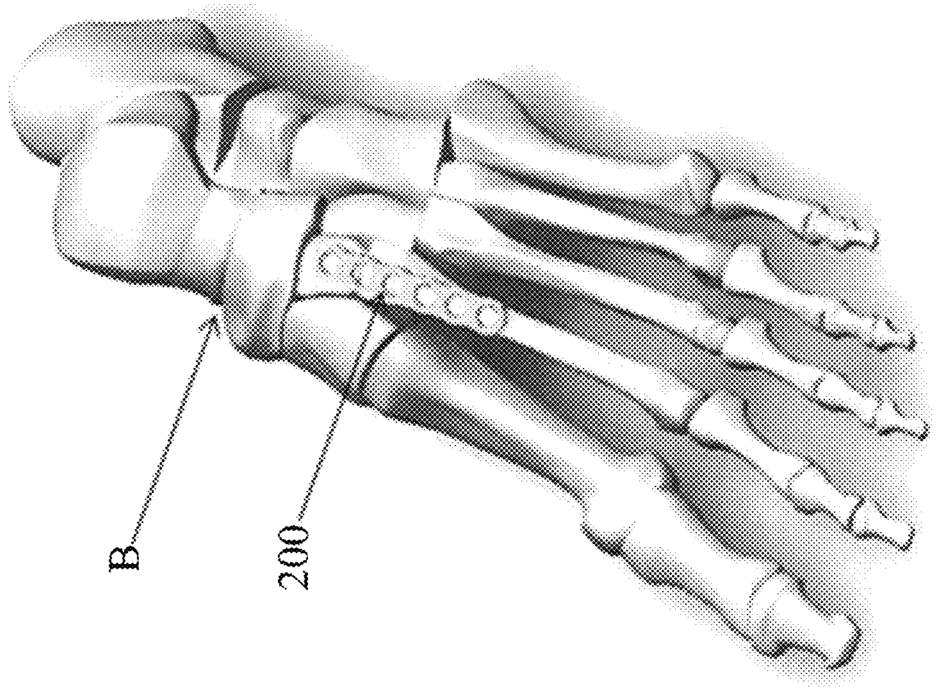
FIG. 7 illustrates the bone plate of FIG. 2 positioned on a bone structure.

The shape, length, width, and/or thickness of body 210 of bone plate 200 is non-limiting. As illustrated in FIGS. 2, 7 and 8, each side of body 210 of bone plate 200 has multiple arcuate regions that create generally wavy side or sinusoidal-shaped edges of the body 210 of bone plate 200. The radius of curvature of the wavy side edges is generally 5-10 mm (and all values and ranges therebetween), and typically 7-9 mm.

The width of body 210 of bone plate 200 can optionally vary along the longitudinal length of body 210 of bone plate 200 as illustrated in 2. The location of screw openings 220 in body 210 of bone plate 200 represents the larger width regions of body 210 of bone plate 200 than the regions absent screw openings 220. In one non-limiting embodiment, the maximum width of body 210 of bone plate 200 (as measured along the lateral axis of the body 210 of bone plate 200) that includes one or more screw openings 220 is 5-40% greater (and all values and ranges therebetween) than the minimum width of the body 210 of bone plate 200 at a location between two screw openings 220.

Fastener arrangement 290 can be any typical, standard locking fastener or a non-locking fastener system. As illustrated in FIGS. 4-6, fastener arrangement 290 is in the form of a screw that includes a head portion 292 and a body portion 294. Body portion 294 includes threads 296. Body portion 294 can be fully or partially threaded. The end of body portion 294 (not shown) can optionally include a self-Lapping or self-drilling tip.

The maximum cross-sectional size of head portion 292 of the screw is greater than the maximum cross-sectional size of body portion 294. The cross-sectional shape of the top region of head portion 292 is generally circular shaped. Head portion 292 can optionally include a cavity 298 to facilitate in inserting the screw into a bone and securing bone plate 200 to bone B as illustrated in FIGS. 7-8. The configuration of cavity 298 is non-limiting. Generally, cavity 298 is specially shaped to receive a tool to rotate and/or otherwise cause the screw to be inserted into a bone B. Non-limiting shapes that can be used in the cavity 298 include one or more dimples, ridges, bumps, textured areas, or any other surface. As illustrated in FIGS. 5 and 6, cavity 298 has a star shape. The depth of cavity 298 is generally less the longitudinal length of head portion 292 as illustrated in FIG. 6.

Figure 9:
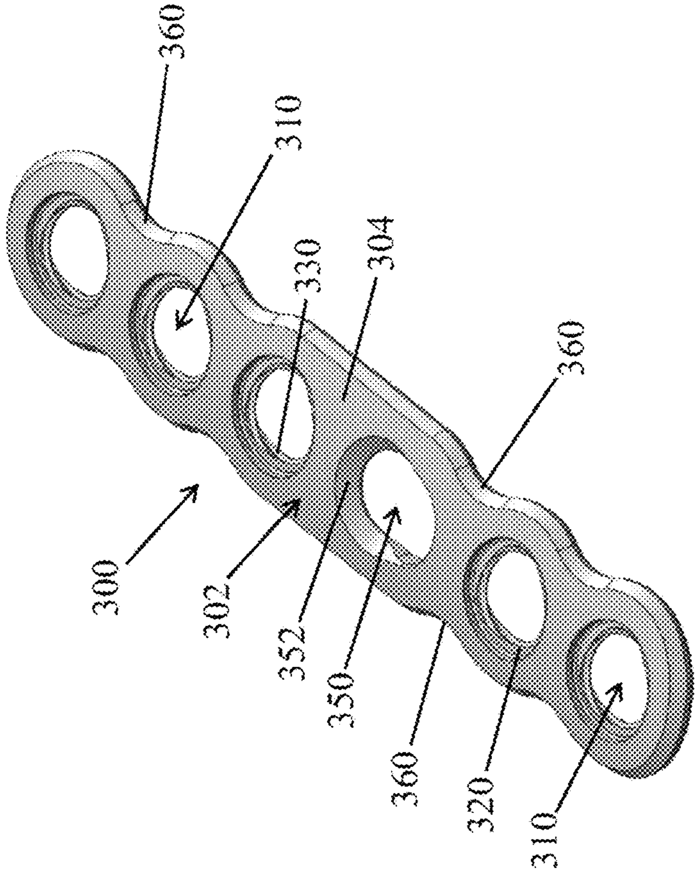
FIG. 9 is an elevation top view of another non-limiting embodiment of the bone plate in accordance with the present disclosure.
Figure 10:
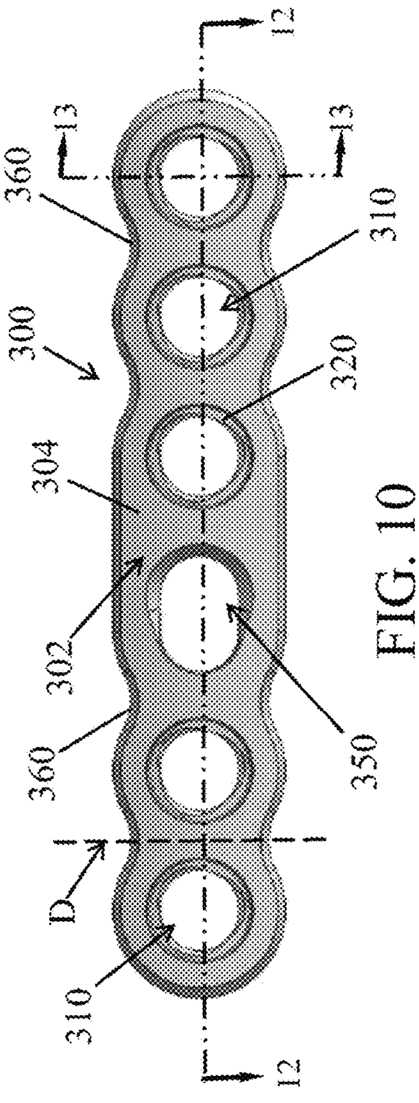
FIG. 10 is a top plan view of the bone plate of FIG. 9.

Referring now to FIGS. 9-23, another embodiment of the bone plate and fastener arrangement is illustrated. As illustrated in FIGS. 9-13, there is illustrated bone plate 300 in accordance with the present disclosure. Bone plate 300 is configured to provide a bone fixation assembly that can accept a fastener arrangement 400 (e.g., screws, etc.). Bone plate 300 has a body 302 that has a lower surface 306 and an upper surface 304, a central longitudinal axis as represented by dashed line 12 of FIG. 10, a lateral axis that is traverse to the central longitudinal axis as represented by dashed line 13 of FIG. 10, and one or more screw openings 310 that extend from lower surface 306 to upper surface 304. Each of the screw openings 310 has a central longitudinal axis. The central longitudinal axis C of the far-right screw opening 350 of FIGS. 10 and 12 is represented by the intersection of axis lines 12 and 13 in FIG. 10 and line C of FIG. 12. Bone plate 300 is illustrated has including five (5) screw openings 310 and a central opening 350 which can be formed into a screw opening or can be formed into an opening that temporarily secures bone plate 300 in place and/or facilitates in the positioning of the bone plate 300 in position on a bone. The number of screw openings 310 in bone plate 300 is non-limiting (e.g., 2-10 and all values and ranges therebetween).

The shape and/or size of screw openings 310 can be the same or different. As illustrated in FIGS. 9-12, the shape and size of all of screw openings 310 are the same. The spacing of adjacently positioned screw openings 310 can be the same or different. As illustrated in FIGS. 9-12, the spacing of adjacently positioned screw openings 310 are the same. The screw openings 310 are spaced from the peripheral edge of bone plate 300. As best illustrated in FIG. 10, screw openings 310 are aligned along the central longitudinal axis of bone plate 300; however, this is not required. The spacing of adjacently positioned screw openings 310 can be the same; however, this is not required. The minimum spacing of each of screw openings 310 from the outer perimeter edge of bone plate 300 can be the same; however, this is not required. Generally, the spacing of the screw openings 310 from the outer perimeter edge of bone plate 300 is at least 0.015 inches (e.g., 0.015-0.1 inches and all values and ranges therebetween), and typically at least 0.03 inches.

Figure 11:
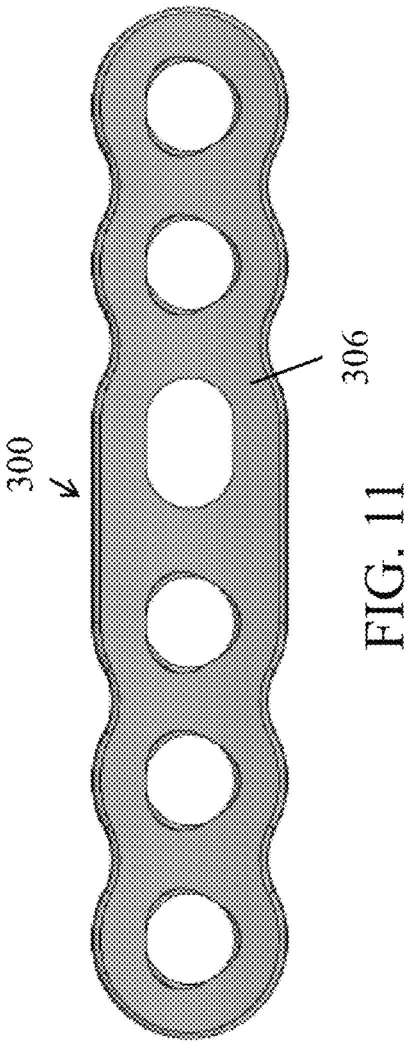
FIG. 11 is a bottom plan view of the bone plate of FIG. 9.
Figure 12:
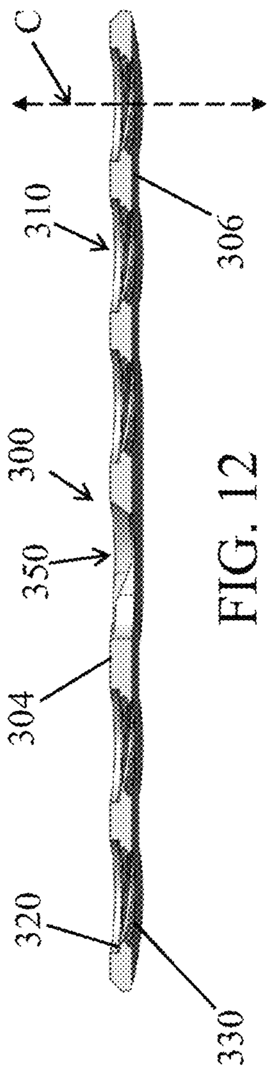
FIG. 12 is a cross-sectional view of the bone plate along line 12-12 of FIG. 9.

Referring now to FIGS. 10-11, the sides of bone plate 300 are illustrated as including indent regions 360 located in between screw openings 310, thereby causing the width of bone plate 300 to vary along the longitudinal length of the bone plate. The depth of the indent regions (when used) is non-limiting. As illustrated in FIGS. 9-11, a non-indented region exists between one of screw openings 310 and central opening 350; however, this is not required.

The thickness of bone plate 300 is at least 0.02 inches (e.g., 0.02-0.1 inches and all values and ranges therebetween), and typically at least 0.3 inches As illustrated in FIGS. 9 and 12, bone plate 300 is substantially linear (e.g., 0-5° and all values and ranges therebetween) along the longitudinal axis of bone plate 300; however, this is not required.

As illustrated in FIGS. 9-11, the width of bone plate 300 varies along the longitudinal length of bone plate 300. Both sides of the bone plate are illustrated as having multiple arcuate regions 360 that create a generally wavy side or sinusoidal-shaped edges of bone plate 300. The radius of curvature of the wavy side edges is generally 5-10 mm (and all values and ranges therebetween), and typically 7-9 mm. Due to these arcuate regions 360, the width of bone plate 300 varies along the longitudinal length of bone plate 300. Generally, the location of screw openings 310 in bone plate 300 represents a larger width region of bone plate 300 than the regions absent screw openings 310. Generally, the maximum width of bone plate 300 (as measured along the lateral axis of the bone plate) that includes one or more screw openings 310 (e.g., along line 13 of FIG. 10) is 5-40% greater (and all values and ranges therebetween) than the minimum width of bone plate 300 at a location between two screw openings 310 (e.g., along line D of FIG. 10).

Figure 13:
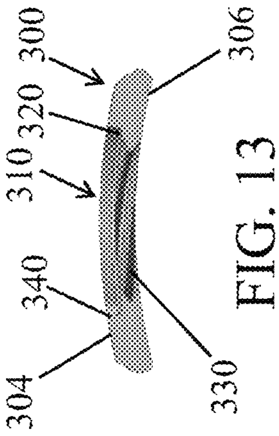
FIG. 13 is a cross-sectional view of the bone plate along line 13-13 of FIG. 9.

As illustrated in FIG. 13, bone plate 300 has a curved profile (e.g., 1-15 and all values and ranges therebetween) along the lateral axis of the bone plate and about the central longitudinal axis of bone plate 300; however, this is not required.

Figure 21:
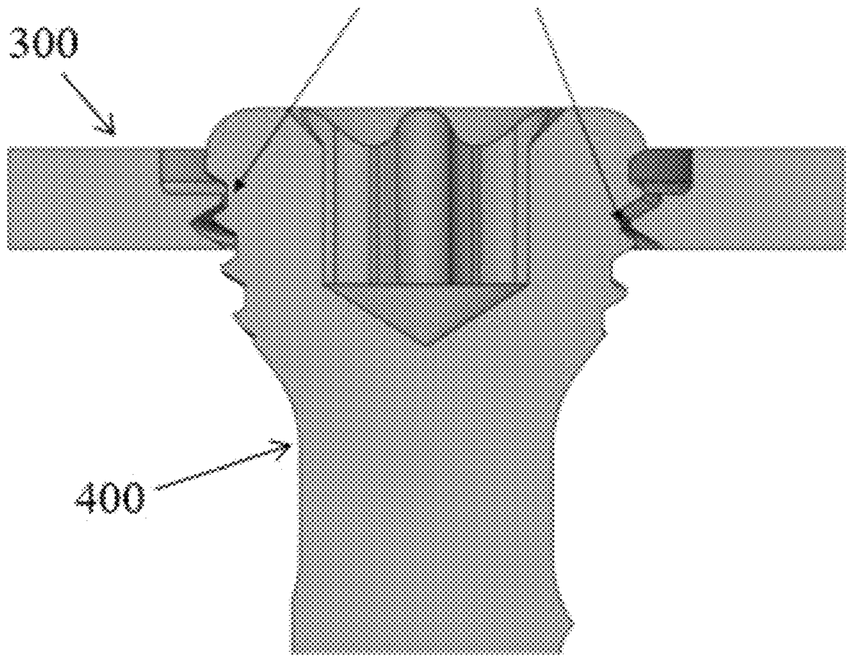
FIG. 21 is a side cross-sectional view of the top portion of the bone plate of FIG. 9 with a screw partially inserted in the screw openings of the bone plate.
Figure 22:
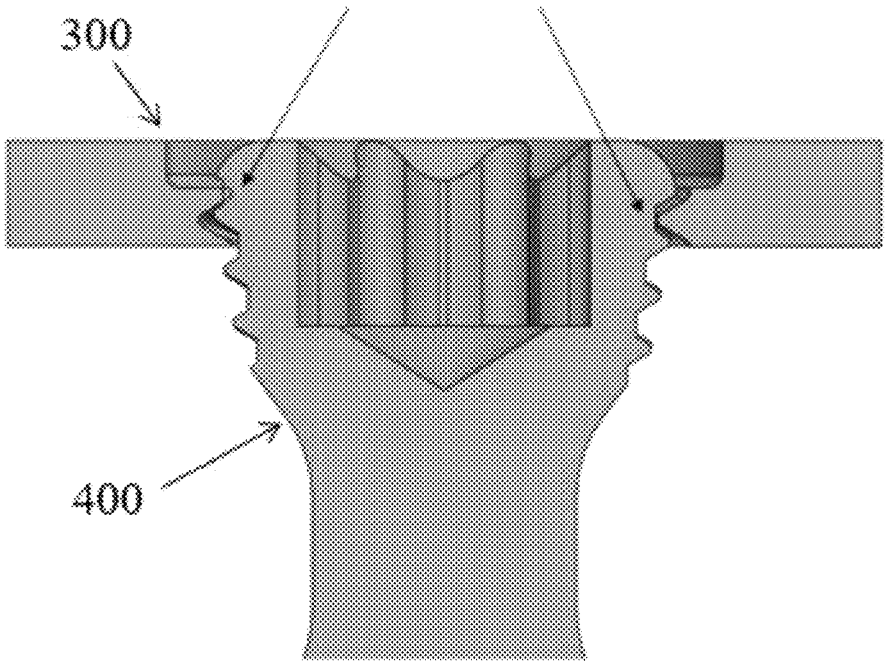
FIG. 22 is a side cross-sectional view of the top portion of the bone plate of FIG. 9 with a screw fully inserted in the screw openings of the bone plate.
Figure 23:
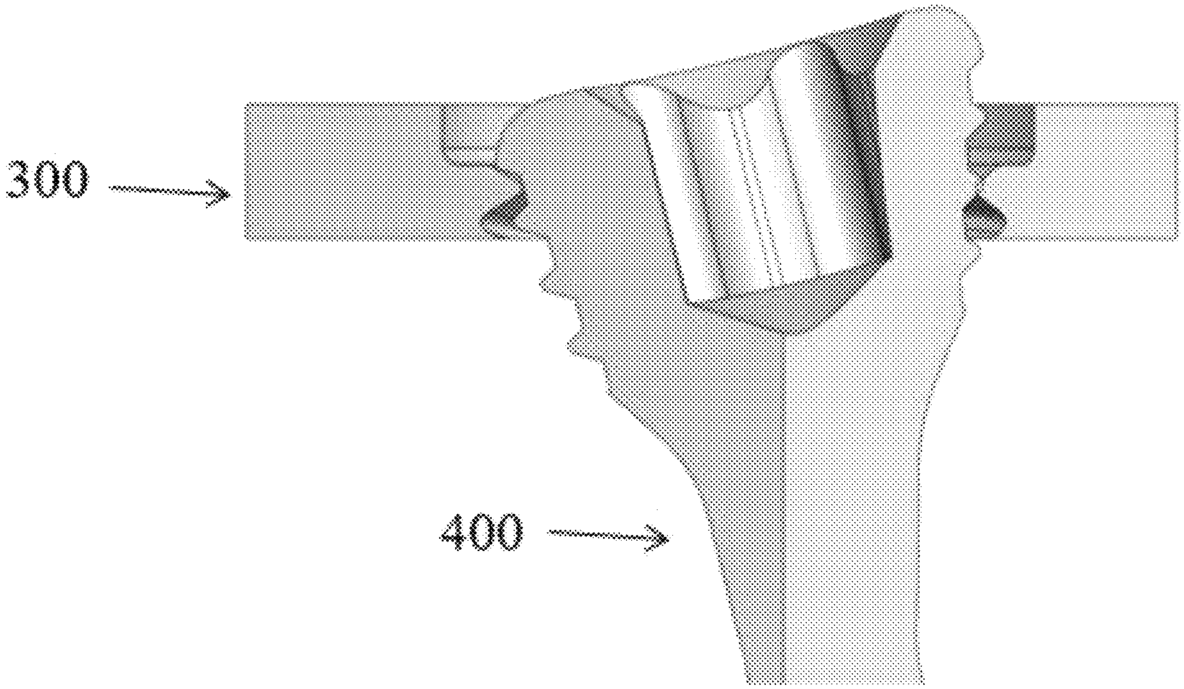
FIG. 23 is a side cross-sectional view of the top portion of the bone plate of FIG. 9 with a screw fully inserted in the screw openings of the bone plate at a different orientation than in FIG. 22.

The one or more screw openings 350 in body 302 of bone plate 300 are shown as having a central longitudinal axis C as illustrated in FIG. 12, and screw openings 350 are adapted to receive fastener arrangement 400 as illustrated in FIGS. 21-23.

Referring now to FIGS. 9-13 and 20-23, the inner surface of the one or more screw openings 310 has a special threaded configuration that enables head portion 410 of fastener arrangement 400 to be locked in screw opening 310 once head portion 410 of fastener arrangement 400 is partially or fully inserted into screw opening 310.

Figure 20:
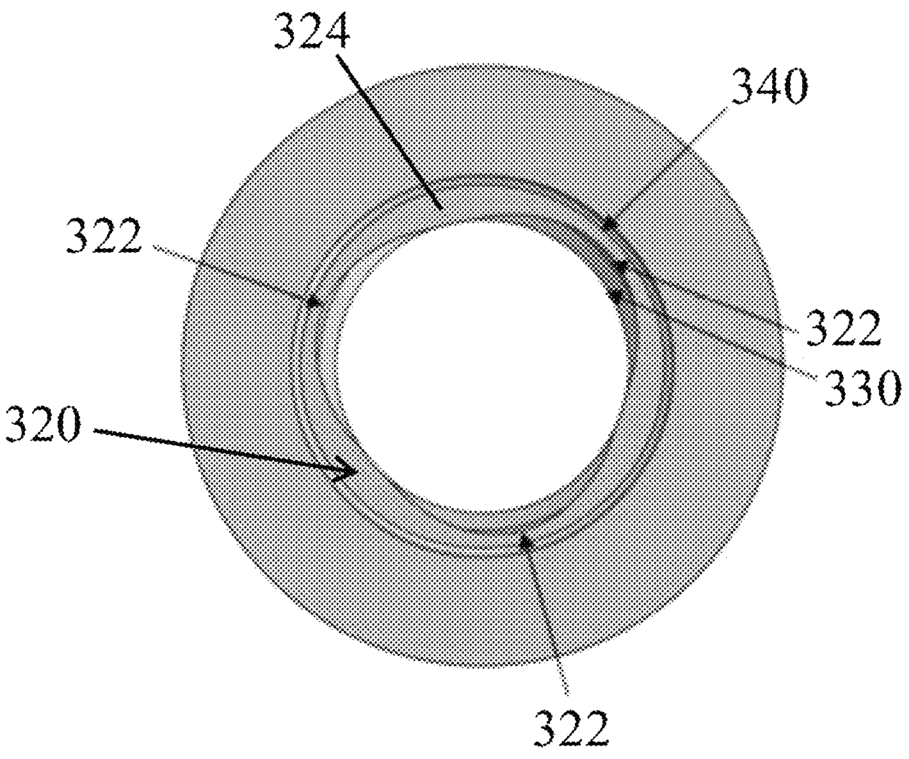
FIG. 20 is an enlarged top plan view of one opening in the bone plate of FIG. 9.

Screw openings 310 include a lead thread plate 320 that includes a plurality of lead recesses 322 (e.g., 2-6 lead recesses, 3 lead recesses, etc.), and wherein lead recesses 322 are spaced from one another by wide portions 324. The plurality of lead recesses 322 are configured to facilitate in the threading of head portion 410 of the fastener arrangement 400 to screw opening 310. As illustrated in FIG. 20, the minimum width of one or more of the lead recesses 322 is less than a maximum width of bottom threads 330 located below lead thread plate 320. Generally, the maximum width of wide portions 324 of lead thread plate 320 is greater than a maximum width of a bottom thread 330 located below the lead thread plate as illustrated in FIG. 20. The lead recesses 322 and wide portions 324 are illustrated as being spaced at equal distances about screw opening 310; however, this is not required.

As illustrated in FIGS. 12, 13 and 20, lead thread plate 320 is recessed from upper surface 304 of bone plate 300. A recess wall 340 extends upwardly from the upper surface of lead thread plate 320 to upper surface 304 of bone plate 300. The shape of the recessed region having an outer perimeter as defined by recess wall 340 is generally cylindrical; however, this is not required. The depth of the recessed region is at least 0.002 inches (e.g., 0.002-0.025 and all values and ranges therebetween), and typically at least 0.005 inches. Generally, the depth of the recessed region is at least 5% (e.g., 5-60% and all values and ranges therebetween) of the thickness of screw opening 310, and typically the depth of the recessed region is at least 15% of the thickness of screw opening 310. The recessed region has a generally circular cross-sectional shape; however, this is not required. As illustrated in FIGS. 12 and 13, the maximum cross-sectional area of the recessed region is greater than the maximum cross-sectional area of the recessed region under the lead thread plate that include bottom threads 330. As such, the diameter or cross-sectional area of screw opening 310 located above lead thread plate 320 is greater than the maximum diameter or cross-sectional area of the region that includes threads 330 located below lead thread plate 320. The depth of the recessed region formed by lead thread plate 320 is generally uniform throughout the recessed region. The thickness of lead thread plate 320 is generally the same. In one non-limiting configuration, the top surface of lead thread plate 320 is generally parallel to upper surface 304 of bone plate 300.

Referring now to FIGS. 9, 12 and 13, the inner surface of the one or more screw openings 310 located below lead thread plate 320 includes one or more sets of lower threading 330. The lower threading 320 forms a spiral surface that has a generally uniform thread width and thickness along the depth of the screw opening. In another non-limiting embodiment, one or more of lower threading 320 does not fully encircle the screw opening 310 (e.g., lower threading encircles 30-90% of the screw opening and all values and ranges therebetween) In one non-limiting arrangement, one or more screw openings 310 includes a lead thread plate 320 that includes first, second, and third lead recesses 322 and a first lower thread that begins below the first lead recess, a second lower thread begins below the second lead recess, and a third lower thread begins below the third lead recess, and wherein the first, second, and/or third lower threads optionally do not fully encircle screw opening 310, and wherein lead recesses 322 are optionally spaced equal distances from adjacently positioned lead recesses 322. The longitudinal length of one or more lower threads 330 along central axis C of screw opening 310 is at least 25% (e.g., 25-90% and all values and ranges therebetween) of the thickness of screw opening 310.

As illustrated in FIGS. 12 and 13, the angle between lead thread plate 320 and the beginning of lower thread 330 located below lead thread plate 320 is about 10-40° (e.g., and all values and ranges therebetween); however, other angles can be used.

As illustrated in FIGS. 9 and 10, bone plate 300 includes a non-threaded screw opening 350. Non-threaded screw opening 350 is absent a lead thread plate and a lower thread. Non-threaded screw opening 350 can have a maximum cross-sectional area along the longitudinal length of bone plate 300 that is greater than a maximum cross-sectional area of one or more of screw openings 310 that include a lead thread plate 320 and one or more lower threads 330. Non-threaded screw opening 350 is illustrated as positioned between screw openings 310 that include a lead thread plate 320 and one or more lower threads 330. Non-threaded screw opening 350 has a sloped surface 352 that slopes downwardly from an upper surface 304 of body 302 of bone plate 300. Sloped surface 352 has a thickness of 50-100% (and all values and ranges therebetween) of the thickness of body 302 of bone plate 300, and slope surface 352 does not fully encircle non-threaded screw opening 350.

The configuration of bone plate 300 and/or screw openings 310 in bone plate 300 can be configured to enable a fastener arrangement 400 to be oriented a) along central axis C of screw opening 310 when fully inserted into the screw opening 310, or b) be oriented off-center from central axis C of screw opening 310 when fully inserted into the screw opening. Bone plate 300 having a plurality of screw openings 310 with the same size and configuration can enable a) all of the fastener arrangements 400 to be oriented in the same way relative to central axis C of screw opening 310 when fully inserted into the screw openings 310, or b) one or more of fastener arrangements 400 have a different orientation to other fastener arrangements 400 when fully inserted into screw openings 310.

Bone plate 300 having a plurality of screw openings 310 with the same size and configuration can also enable a) central axis C of all of fastener arrangements 400 to be parallel with one another when fully inserted into screw openings 310, or b) central axis C of one or more of fastener arrangements 400 to be non-parallel (e.g., oriented inwardly toward one another, oriented outwardly from one another, etc.) with central axis C of one or more other fastener arrangements 400 when fully inserted into screw openings 310.

The ability to enable the fastener arrangements to have the ability to be secured to the bone plate in various orientations relative to the central axis of the bone while using the same screw opening configuration on the bone plate is a significant advantage when attempting to secure the bone plate to a bone since the desired location of insertion of the fastener arrangement to the bone when the bone plate is positioned on the bone is not always along the central axis of the screw opening. The ability to custom orient the fastener arrangement relative to the central axis of one or more or all of the screw openings enables the proper insertion of the fastener arrangement in the bone once the bone plate is properly positioned on the bone.

Referring now to 14-23, fastener arrangement 400 is in the form of a screw. The fastener arrangement 400 includes a head portion 410 and a body portion 440 connected to the bottom of head portion 410 and extends downwardly from head portion 410.

Head portion 410 includes a top opening 420 and head threading 430 on the outer surface of head portion 410.

Figure 14:
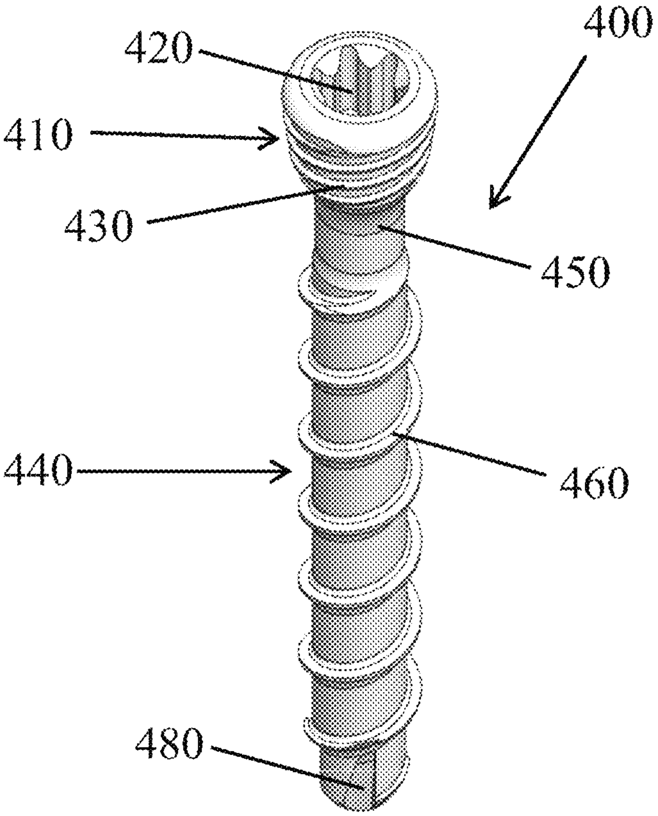
FIG. 14 is a side elevation view of a screw in accordance with the present disclosure.
Figure 15:
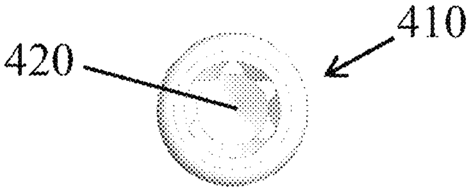
FIG. 15 is a top view of the screw of FIG. 14.
Figure 16:
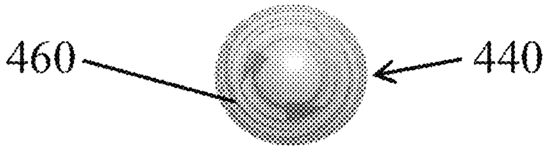
FIG. 16 is a bottom view of the screw of FIG. 14.

Top opening 420 generally includes a non-circular cross-sectional shape or a threaded inner surface. As illustrated in FIGS. 14 and 15, top opening 420 has a hexagonal cross-sectional shape along at least a portion of the central axis of opening 420. As can be appreciated, other non-circular cross-sectional shapes can be used (e.g., triangular, square, polygonal, oval, etc.). As illustrated in FIGS. 21-22, the depth of top opening 420 along the central axis of top opening 420 is generally at least 30% (e.g., 30-100% and all values and ranges therebetween) the depth of head portion 410 along the central axis of head portion 410. Top opening 420 is generally spaced from the other perimeter of head portion 410.

Head portion 410 has a tapered profile along the central axis of head portion 410. The angle α of taper is generally at least 1° (e.g., 1-25° and all values and ranges therebetween) In one non-limiting configuration, the angle of taper of head portion 410 is 10-20°. As such, the cross-sectional area and/or diameter of the top of head portion 410 is greater than the cross-sectional area and/or diameter of the bottom of head portion 410. As illustrated in FIGS. 17, 18, 21 and 22, the cross-sectional area and/or diameter of head threading 430 from the top to the bottom of head 410 portion also progressively reduces due to the taper of the head portion.

The tapered profile includes head threading 430 along 60-100% (and all values and ranges therebetween) of the central axis of the tapered portion of the head portion. The tapered portion of the head portion is generally 20-100% (and all values and ranges therebetween) of the longitudinal length of the head portion. The angle of taper of the head portion can be constant along 60-100% (and all values and ranges therebetween) of the taper. Head threading 430 on the head portion 410 is spirally shape and has a) a constant width along 60-100% (and all values and ranges therebetween) the length of the threading, b) a constant shape along 60-100% (and all values and ranges therebetween) the length of the threading, c) a constant lead along 60-100% (and all values and ranges therebetween) the length of the threading, and/or d) a constant pitch along 60-100% (and all values and ranges therebetween) the length of the threading.

The use of the tapered region on the head portion of the fastener arrangement can optionally facilitate in enabling in the fastener arrangement to be oriented in the screw opening at a desired angle relative to the central axis of the screw opening. When the screw opening includes a lead thread plate that has two or more recesses, the bottom narrower portion of the taper region of the head portion of the fastener arrangement can be used to allow the fastener arrangement to be angled and positioned in the desired recess of the lead thread plate of the screw opening before the threads on the taper region fully engage the lead thread plate and/or the threads below the lead thread plate.

Head threading 430 generally has the same or similar pitch as lower threads 330 in screw opening 310 of bone plate 300. The lead of head threading 430 is generally greater than the pitch of head threading 430; however, this is not required. In one non-limiting embodiment, the lead of head threading 430 is about 0.04-0.1 inches (and all values and ranges therebetween), and the pitch of head threading 430 is about 0.01-0.05 inches (and all values and ranges therebetween). In one non-limiting specific configuration, the lead is about 0.06 inches and the pitch is about 0.02 inches. Head threading 430 is illustrated as encircling head portion 410 at least once (e.g., 1-6 encirclements of head portion 410 and all values and ranges therebetween).

The angle of head threading 430 is generally the same or similar to the angle of lower thread 330 located below lead thread plate. In one non-limiting configuration, the angle of head threading 430 is about 60° (e.g., 60°±20° and all values and ranges therebetween); however, other angles can be used.

Head portion 410 generally has a maximum cross-sectional area that is greater than a maximum cross-sectional area of body portion 440. The shape of head portion 410 is non-limiting. In one non-limiting configuration, the cross-sectional shape of the top region of head portion 410 is generally circular shaped.

Figure 17:
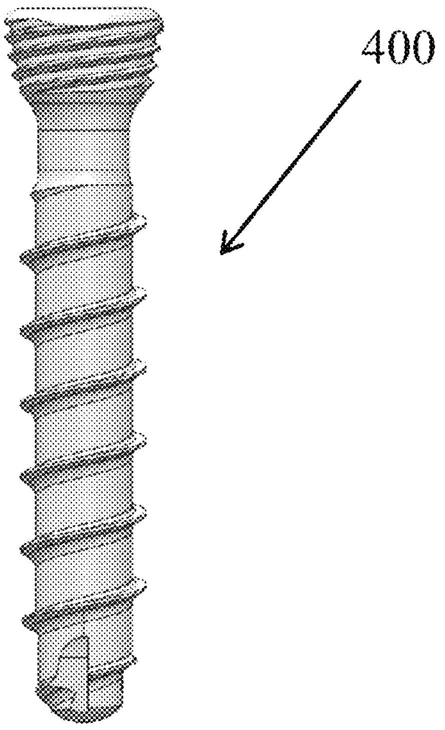
FIG. 17 is a side view of the screw of FIG. 14.
Figure 18:
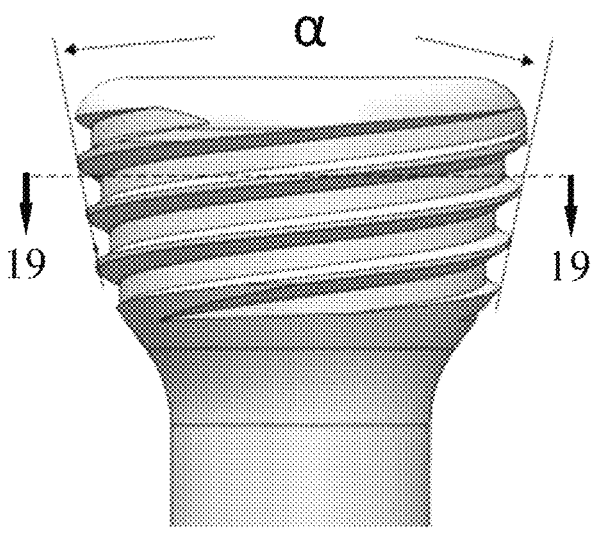
FIG. 18 is an enlarged side view of a top portion of the screw of FIG. 14.
Figure 19:
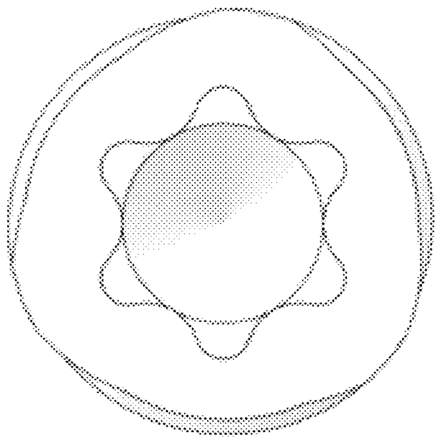
FIG. 19 is a cross-sectional view of the head of the screw along line 19-19 of FIG. 18.

As illustrated in FIGS. 14, 17 and 18, fastener arrangement 400 can optionally include a transition portion 450 that is located from the bottom portion of head portion 410 to the top of body portion 440; however, this is not required. Transition portion 450 (when used) can include one or more curved regions; however, this is not required. The non-threaded transition region of the head portion (when used) is generally 5-80% (and all values and ranges therebetween) of the longitudinal length of the head portion. In one non-limiting configuration, the minimum cross-sectional area of the non-threaded transition region is less than the maximum cross-sectional area of the head portion and/or the body portion, and the non-threaded transition region has a generally circular cross-sectional shape along 60-100% (and all values and ranges therebetween) of the longitudinal length of non-threaded transition region 450. The use of the non-threaded transition region on the head portion of the fastener arrangement optionally facilitate in enabling the fastener arrangement to be oriented in the screw opening at a desired angle relative to the central axis of the screw opening. When the screw opening includes a lead thread plate that has two or more recesses, the non-threaded transition region of the head portion of the fastener arrangement can be used to allow the fastener arrangement to be angled and positioned in the desired recess of the lead thread plate of the screw opening before the threads on the taper region fully engage the lead thread plate and/or the threads below the lead thread plate.

Referring now to FIGS. 14 and 17, body portion 440 of fastener arrangement 400 includes body threading 460 that is configured to be secured into a bone. Body threading 460 generally has a different lead and pitch than head threading 430 of fastener arrangement 400. In one non-limiting configuration, head threading 430 of fastener arrangement 400 has a lead of 0.04-0.08 inches (and all values and ranges therebetween) and a pitch of 0.01-0.04 inches (and all values and ranges therebetween) and a thread angle of 30-70° (and all values and ranges therebetween). Head threading 430 is illustrated as being a single thread. The pitch of body threading 460 is generally greater than the pitch of head threading 430 (e.g., at least 20% greater) In one non-limiting configuration pitch of body threading 460 is 0.05-0.12 inches. The lead of body threading 460 is generally greater than the lead of head threading 430 (e.g., at least 20% greater). In one non-limiting configuration lead of body threading 460 is 0.05-0.12 inches.

Head threading 430 can have the same or similar lead and pitch as lower threading 330 in screw opening 310.

Body threading 460 on the body portion of the fastener arrangement has a maximum cross-sectional area that is less than the minimum cross-sectional area of screw opening 310 so the body portion of the fastener arrangement can be passed through the screw opening.

As illustrated in FIG. 17, body threading 460 on the body portion of the fastener arrangement has a maximum cross-sectional area that is less than the maximum cross-sectional area of head threading 430.

The bottom portion of body portion 440 optionally includes a cut face 480 that can be used to facilitate in the tip of fastener arrangement 400 penetrating into a bone.

Referring now to FIGS. 21-23, there is illustrated fastener arrangement 400 that has been threaded into bone plate 300. FIGS. 21 and 22 illustrate fastener arrangement 400 as being threadedly secured to bone plate 300 and the central axis of fastener arrangement 400 is generally perpendicular to the longitudinal axis of bone plate 300. FIG. 22 illustrates fastener arrangement 400 as being threadedly secured to bone plate 300 and the central axis of fastener arrangement 400 is non-perpendicular to the longitudinal axis of bone plate 300. In both of these configurations, fastener arrangement 400 is able to be locked in position relative to bone plate 300. The tapered profile of head portion 410 enables fastener arrangement 400 to be inserted along central axis C of screw opening 310, or positioned at some non-parallel angle relative to central axis C of screw opening 310 when initially orienting fastener arrangement 400 relative to screw opening 310. One the desired orientation of fastener arrangement 400 relative to the screw opening is obtained, the fastener arrangement can then be threaded into screw opening 310 to thereby secure and lock the fastener arrangement in position relative to bone plate 300. FIG. 21 illustrates the fastener arrangement inserted into the screw opening prior to full insertion and FIG. 22 illustrated that fastener arrangement fully inserted into the screw opening and locked in the screw opening.

The locking of fastener arrangement 400 in screw opening 310 is at least in part achieved when the top of body threading 460 is positioned below lead thread plate 320. When head portion 410 of the fastener arrangement 400 is inserted sufficient in the screw opening 310 such that some or all of the top of body threading 460 is positioned below lead thread plate 320, the fastener arrangement becomes locked in the screw opening from lead thread plate 320 resisting fastener arrangement 400 from being threaded out from screw opening 310.

Turning now to the methods of implantation, the surgeon accesses the surgical site of interest, which can be an internal site at which a bone fracture that requires stabilization to ensure proper healing is located. The fracture may be reduced with conventional forceps and guides (which are known to those in the art), and a bone plate of appropriate size and shape is placed over the fracture site. In some instances, the bone plate may be temporarily secured to the bone using provisional fixation pins. When used, provisional fixation pins may be used through any of the openings in the bone plate. Provisional fixation pins temporarily secure the bone plate to the bone before placing the fastener system (e.g., screws, etc.) through the opening in the bone plate. Thus, the surgeon can be certain that the bone plate is properly positioned before placing the fastener system for permanent fixation of the bone plate to the bone.

Once the bone plate is secured at a desired location in relation to the fracture, the surgeon then identifies an insertion angle, or the direction along which the fastener system is to be inserted through one or more openings in the bone plate and then driven into the bone material of the bone. If the bone plate includes more than one opening, the surgeon also selects the specific openings in the bone plate to be used. After selecting the desired insertion angle and openings to be used in the bone plate, the surgeon inserts a lower portion of the fastener system through each of the selected openings in the bone plate until the bottom of the fastener system contacts bone material. In some cases, a hole may need to be drilled or tapped into the bone along the insertion angle to facilitate the initial tapping or insertion of the fastener system into the bone. The surgeon then uses an appropriate driving tool in the cavity of the head portion of the fastener system to manipulate the fastener system into place.

The fastener system can optionally be inserted at angles other than being aligned with the central axis of the opening in the bone plate. In some instance, the surgeon may need to toggle or maneuver the fastener system in order to secure and draw in displaced bone fragments during the securing of the bone plate to the bone.

Once the bone fragment is secured, the fastener system is ready to be secured to the bone plate. As the fastener system is driven further into bone, it is also drawn further into the bone plate.

With reference to the non-limiting embodiment of FIGS. 2-8, as the head portion of the fastener system begins to contact protruding surfaces 230 in screw opening 220 in the bone plate, one or more of protruding surfaces 230 are caused to at least partially plastically deform and thereby secure the head portion of the fastener arrangement to the bone plate in the desired angle. The action of engagement between the protruding surfaces and the fastener arrangement rigidly affixes the fastener arrangement to the bone plate. In some embodiments, the surgeon can optionally use traditional locking and/or non-locking screws in one or more other openings in the bone plate. This can potentially help further secure the bone plate to the bone fracture if needed.

With reference to the non-limiting embodiment of FIGS. 9-23, head portion 410 of fastener arrangement 400 is inserted further into the screw openings of bone plate 300. The angular shape of the head portion in combination with the threading on the head portions and the threading on the bone plate results in the locking screw locking into position relative to the bone plate.

In one optional procedure, once all fastener systems are inserted into the bone plate, the surgeon may optionally place covers over the unused openings in the bone plate. Additionally or alternatively, the surgeon may use bone graft material, bone cement, bone void filler, and any other material to help heal the bone. Such material (when used) can be placed in one or more unused openings in the bone plate and/or placed one and/or about one or more portions of the bone plate.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment, or "in an embodiment" in places throughout the specification are not necessarily all referring to the same embodiment. Furthermore, the particular features, structures or characteristics may be combined in any suitable manner in one or more embodiments.

It will thus be seen that the objects set forth above, among those made apparent from the preceding description, are efficiently attained, and since certain changes may be made in the constructions set forth without departing from the spirit and scope of the disclosure, it is intended that all matter contained in the above description and shown in the accompanying drawings shall be interpreted as illustrative and not in a limiting sense. The disclosure has been described with reference to preferred and alternate embodiments. Modifications and alterations will become apparent to those skilled in the art upon reading and understanding the detailed discussion of the disclosure provided herein. This disclosure is intended to include all such modifications and alterations insofar as they come within the scope of the present disclosure. It is also to be understood that the following claims are intended to cover all of the generic and specific features of the disclosure herein described and all statements of the scope of the disclosure, which, as a matter of language, might be said to fall there between. The disclosure has been described with reference to the certain embodiments. These and other modifications of the disclosure will be obvious from the disclosure herein, whereby the foregoing descriptive matter is to be interpreted merely as illustrative of the disclosure and not as a limitation. It is intended to include all such modifications and alterations insofar as they come within the scope of the appended claims.

To aid the Patent Office and any readers of this application and any resulting patent in interpreting the claims appended hereto, Applicant does not intend any of the appended claims or claim elements to invoke 35 U.S.C. 112(f) unless the words "means for" or "step for" are explicitly used in the particular claim.

What is claimed:

1. An orthopedic fixation device for use in fracture fixation comprising a bone plate body that has a plurality of screw openings therethrough; each of said screw openings has a top and bottom edge that are spaced from one another; at least one of said screw openings as viewed along a central longitudinal axis of said screw opening has a plurality of plastically deformable protruding structures and a plurality of arcuate recessed regions; each of said arcuate recessed regions is located between two protruding structures; each arcuate recessed region forms a side of adjacently positioned protruding structures that the arcuate recessed region is located therebetween; an interior of said screw openings is absent threads; each of said protruding structures includes a top and bottom sloped surface; said top sloped surface extends directly from said top edge of said screw opening to a position located between said top edge and said bottom edge; said bottom sloped surface extends directly from said bottom edge of said screw opening to a position located between said top edge and said bottom edge; each of said top and bottom sloped surfaces have a tapering width; said width of said top sloped surface is largest at said top edge of said screw opening; said width of said bottom sloped surface is largest at said bottom edge of said screw opening; said top and bottom sloped surfaces terminate at an end of said protruding structure to form a pointed end.

2. The orthopedic fixation device as defined in claim 1, wherein each of said protruding structures extend no more than 10% about a perimeter of said screw opening; each of said arcuate recessed regions extends no more than 10% about said perimeter of said screw opening.

3. The orthopedic fixation device as defined in claim 1, wherein each of said top sloped surfaces slopes downwardly from said top edge said screw opening and terminates at a location that is ±0-20% a mid-depth of said screw opening; each of said bottom sloped surfaces slopes upwardly from said bottom edge of said screw opening and terminates at a location that is ±0-20% said mid-depth of said screw opening.

4. The orthopedic fixation device as defined in claim 1, wherein each of said top sloped surfaces is positioned above said bottom sloped surfaces; said top and bottom sloped surfaces each have a same shape and size.

5. The orthopedic fixation device as defined in claim 4, wherein each of said top and bottom sloped surfaces have three sides; each of said arcuate recessed regions includes an intermediate sloped surface that has four sides; each of said arcuate recessed regions has first and second corners wherein said first corner terminates at said pointed end of one of said protruding structures and said second corner terminates at said pointed end of an adjacently positioned protruding structure.

6. The orthopedic fixation device as defined in claim 1, wherein each of said deformable protruding structures and each of said arcuate recessed regions are symmetrically oriented about an outer perimeter of said screw opening.

7. The orthopedic fixation device as defined in claim 1, wherein said bone plate body includes multiple arcuate regions on each side of said bone plate body along a longitudinal length of said bone plate body such that a width of said bone plate body varies along said longitudinal length of said bone plate body; a location of said screw openings in said bone plate body represents a larger width of said bone plate body than regions of said bone plate body that are absent said screw openings.

8. The orthopedic fixation device as defined in claim 1, wherein said bone plate body is at least partially formed of a refractory alloy or a metal alloy that includes at least 15 awt. % rhenium.

9. An orthopedic fixation device for use in fracture fixation comprising a bone plate body that has a plurality of screw openings therethrough; each of said screw openings has a top and bottom edge that are spaced from one another; at least one of said screw openings as viewed along a central longitudinal axis of said screw opening has a plurality of plastically deformable protruding structures and a plurality of arcuate recessed regions; each of said arcuate recessed regions is located between two protruding structures; each arcuate recessed region forms a side of adjacently positioned protruding structures that the arcuate recessed region is located therebetween; an interior of said screw openings is absent threads; each of said protruding structures includes a top and bottom sloped surface; said top sloped surface extends directly from said top edge of said screw opening to a position located between said top edge and said bottom edge; said bottom sloped surface extends directly from said bottom edge of said screw opening to a position located between said top edge and said bottom edge; each of said top and bottom sloped surfaces have a tapering width; said width of said top sloped surface is largest at said top edge of said screw opening; said width of said bottom sloped surface is largest at said bottom edge of said screw opening; each of said arcuate recessed regions has first and second corners wherein said first corner terminates at a pointed end of one of said protruding structures and said second corner terminates at a pointed end of an adjacently positioned protruding structure; each of said protruding structures extend no more than 10% about a perimeter of said screw opening; each of said arcuate recessed regions extends no more than 10% about said perimeter of said screw opening; said bone plate body includes multiple arcuate regions on each side of said bone plate body along a longitudinal length of said bone plate body such that a width of said bone plate body varies along said longitudinal length of said bone plate body; a location of said screw openings in said bone plate body represents a larger width of said bone plate body than regions of said bone plate body that are absent said screw openings.

10. The orthopedic fixation device as defined in claim 9, wherein each of said top sloped surfaces slopes downwardly from said top edge of said screw opening and terminates at a location that is ±0-20% a mid-depth of said screw opening; each of said bottom sloped surfaces slopes upwardly from said bottom edge of said screw opening and terminates at a location that is ±0-20% said mid-depth of said screw opening; each of said top sloped surfaces is positioned above said bottom sloped surfaces; said top and bottom sloped surfaces each have a same shape and size.

11. The orthopedic fixation device as defined in claim 10, wherein each of said top and bottom sloped surfaces have three sides; each of said arcuate recessed regions includes an intermediate sloped surface that has four sides.

12. The orthopedic fixation device as defined in claim 11, wherein a thickness of an end of each of said protruding structures is thinner than at other regions of said protruding structures; a thickest region of said protruding structures is located adjacent an inner wall of said screw opening; a thickness of said protruding structures progressively decreases from a location adjacent said inner wall of said screw opening to said end of said protruding structures located closest to a central axis of said screw opening; said deformable protruding structures and said arcuate recessed regions are symmetrically oriented about an outer perimeter of said screw opening.

* * * * *